United States Patent
Blanco et al.

(10) Patent No.: US 11,253,526 B2
(45) Date of Patent: Feb. 22, 2022

(54) NANOSTRUCTURED FORMULATIONS FOR THE DELIVERY OF SILIBININ AND OTHER ACTIVE INGREDIENTS FOR TREATING OCULAR DISEASES

(71) Applicant: DISTRETTO TECNOLOGICO SICILIA MICRO E NANO SISTEMI S.C.A.R.L., Catania (IT)

(72) Inventors: Anna Rita Blanco, Acireale (IT); Maria Luisa Bondi', Trabia (IT); Gennara Cavallaro, Palermo (IT); Grazia Maria Letizia Consoli, San Gregorio di Catania (IT); Emanuela Fabiola Craparo, Palermo (IT); Gaetano Giammona, Palermo (IT); Mariano Licciardi, Palermo (IT); Giovanna Pitarresi, Palermo (IT); Guiseppe Granata, Acireale (IT); Patrizia Saladino, Santa Ninfa (IT); Clara La Marca, Canicatti' (IT); Irene Deidda, Palermo (IT); Salvatore Papasergi, Taurianova (IT); Patrizia Guarneri, Palermo (IT); Salvatore Cuzzocrea, Viagrande (IT); Emanuela Esposito, Naples (IT); Santa Viola, Paterno' (IT)

(73) Assignee: DISTRETTO TECNOLOGICO SICILIA MICRO E NANO SISTEMI S.C.A.R.L., Catania (IT)

( * ) Notice: Subject to any disclaimer, the term of this patent is extended or adjusted under 35 U.S.C. 154(b) by 0 days.

(21) Appl. No.: 16/984,074

(22) Filed: Aug. 3, 2020

(65) Prior Publication Data
US 2021/0046083 A1 Feb. 18, 2021

Related U.S. Application Data

(62) Division of application No. 15/517,018, filed as application No. PCT/IP2015/057732 on Oct. 9, 2015.

(30) Foreign Application Priority Data

Oct. 9, 2014 (IT) .......................... FI2014AA000230

(51) Int. Cl.
| | |
|---|---|
| A61K 31/5575 | (2006.01) |
| A61K 31/12 | (2006.01) |
| A61K 31/44 | (2006.01) |
| C07C 217/74 | (2006.01) |
| A61K 9/00 | (2006.01) |
| A61K 31/357 | (2006.01) |
| A61K 9/51 | (2006.01) |
| A61K 9/107 | (2006.01) |
| A61K 47/10 | (2017.01) |
| A61K 47/36 | (2006.01) |

(52) U.S. Cl.
CPC ........ *A61K 31/5575* (2013.01); *A61K 9/0048* (2013.01); *A61K 9/107* (2013.01); *A61K 9/5123* (2013.01); *A61K 9/5161* (2013.01); *A61K 31/12* (2013.01); *A61K 31/357* (2013.01); *A61K 31/44* (2013.01); *A61K 47/10* (2013.01); *A61K 47/36* (2013.01); *C07C 217/74* (2013.01); *C07C 2603/92* (2017.05)

(58) Field of Classification Search
None
See application file for complete search history.

(56) References Cited

U.S. PATENT DOCUMENTS

| | | | |
|---|---|---|---|
| 2011/0142923 A1 | 6/2011 | Mazzone et al. | |
| 2014/0235678 A1 | 8/2014 | Boettger et al. | |

FOREIGN PATENT DOCUMENTS

| | | |
|---|---|---|
| CN | 101554371 A | 10/2009 |
| CN | 101627970 A | 1/2010 |
| CN | 103655214 A | 3/2014 |
| CN | 103655519 A | 3/2014 |
| CN | 102949344 A | 5/2014 |
| CN | 103784421 A | 5/2014 |
| EP | 1293248 A1 | 3/2003 |
| EP | 2392326 A1 | 12/2011 |
| JP | 2011530496 A | 12/2011 |
| JP | 2014518232 A | 7/2014 |
| WO | 2013110050 A1 | 7/2013 |
| WO | 2013171204 A2 | 11/2013 |
| WO | 2014153733 A1 | 10/2014 |

OTHER PUBLICATIONS

Gong Yan, "Changes in retinal oxidative stress level and function in early diabetic rats and the protective effect of silibinin", Wan Fang Data, Jun. 27, 2007, doi 10.7666/d.y651047.
International Search Report of the International Searching Authority, dated Mar. 323, 2018 for corresponding PCT patent application No. PCT/IB2015/057732.
Database WPI Section Ch, Week 201017, Thomson Scientific, London, GB; Class A96, AN 2010-B20081 XP002740561, Duan Z. et al., "Preparation of solid lipid nano-granule medicine involves heating mixture of lipid base material and emulsifier, adding medicine to obtained liquid oil phase, emulsifying formed mixture and reducing temperature".

(Continued)

*Primary Examiner* — Danah Al-Awadi
(74) *Attorney, Agent, or Firm* — Abelman, Frayne & Schwab

(57) ABSTRACT

Formulations are described, containing silibinin or other active ingredients incorporated in lipid nanoparticle systems of the SLN and NLC type, and based on calixarenes, possibly mucoadhesive, or in micellar and nanoparticle systems based on amphiphilic inulin copolymers for use in the treatment of neurodegenerative ocular diseases. The versatility of the calixarene compound is also described, capable of charging and releasing active ingredients characterized by low water solubility, easy chemical and enzymatic degradation, low bioavailability, either of natural origin or not, to be used in the treatment of ocular diseases.

3 Claims, 18 Drawing Sheets

(56) References Cited

OTHER PUBLICATIONS

Zhang H-T et al, "Silybin reduces obliterated retinal capillaries in experimental diabetic retinopathy in rats", European Journal Of PHARMACOLOGY,vol. 740, Oct. 5, 2014 (Oct. 5, 2014), p. 233-239.
Lin CH et al, "Silibinin inhibits VEGF secretion and age-related macular degeneration in a hypoxia-dependent manner through the PI-3 kinase/Akt/mTOR pathway", Br J PHARMACOL,vol. 168, No. 4, Feb. 2013 (Feb. 2013), p. 920-931.
Haider M Mohammed et al., "Effects of silibinin hemisuccinate on the intraocular pressure in normotensive rabbits", Saudi Medical JOURNAL,vol. 28, No. 9, Sep. 1, 2007 (Sep. 1, 2007), p. 1397-1401.
A Seyfoddin et al, "Solid lipid nanoparticles for ocular drug delivery", Drug Delivery,vol. 17, No. 7, 2010, p. 467-489.
Database WPI T Section Ch, Week 200981, Thomson Scientific, London, GB; VXP002740565, M. Huo et al., "Use of amphiphilic polymer carrier to prepare silybin and silymarin polymer micelle solution for improving medical liver targeted property, or improving biological utilization degree of medicine".
Jia Le-Jiao et al, "Preparation and characterization of silybin-loaded nanostructured lipid carriers", Jan. 1, 2010 (Jan. 1, 2010), vol. 17, No. 1, p. 11-18.
S. Thiele et al., "Multikinase Inhibitors as a New Approach in Neovascular Age-Related Macular Degeneration (AMD) Treatment: In Vitro Safety Evaluations of Axitinib, Pazopanib and Sorafenib for Intraocular Use," Klin Monatsbl Augenheikd, 230:247-254 (2013).
Tuan-Phat Huynh, et al., "Botanical Compounds: Effects on Major Eye Disease," Evidence-Based Complementary and Alternative Medicine, 103:1-12 (2013).
James et al., Antioxidant phospholipid cali(4)arene mimics as micellular delivery systems, Org. & Biomol. Chem., 11:6108-6113 (2013).
Liu et al., "Preparation and Quality Control of Silybin Meglumine Ophtalmic Gel," China Pharmacy, 24(33):3123 (2013).
Martin et al., "Synthesis and Toxicology of p-Phosphonic Acid Calixarenes and O-Alkylated Analogues as potential Calixarene-Based Phospholipids," ChemPlusChem, 77:308-312 (2012).
Rodik et al., "Cationic amphiphilic calixarenes to compact DNA into small nanoparticles for gene delivery," New J. Chem., 38:1654 (2015).

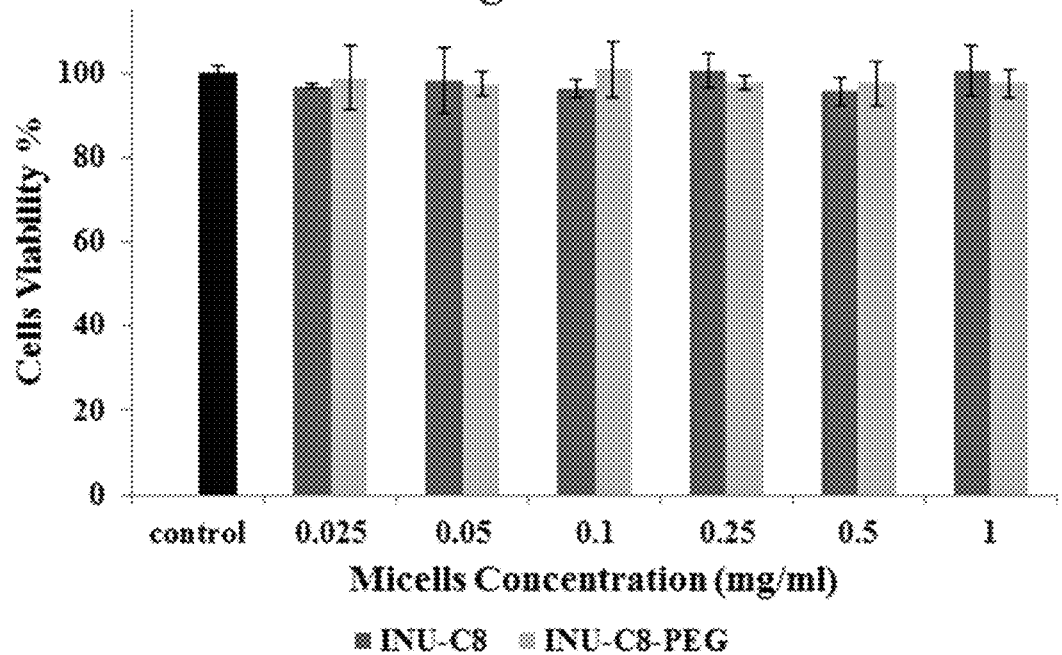
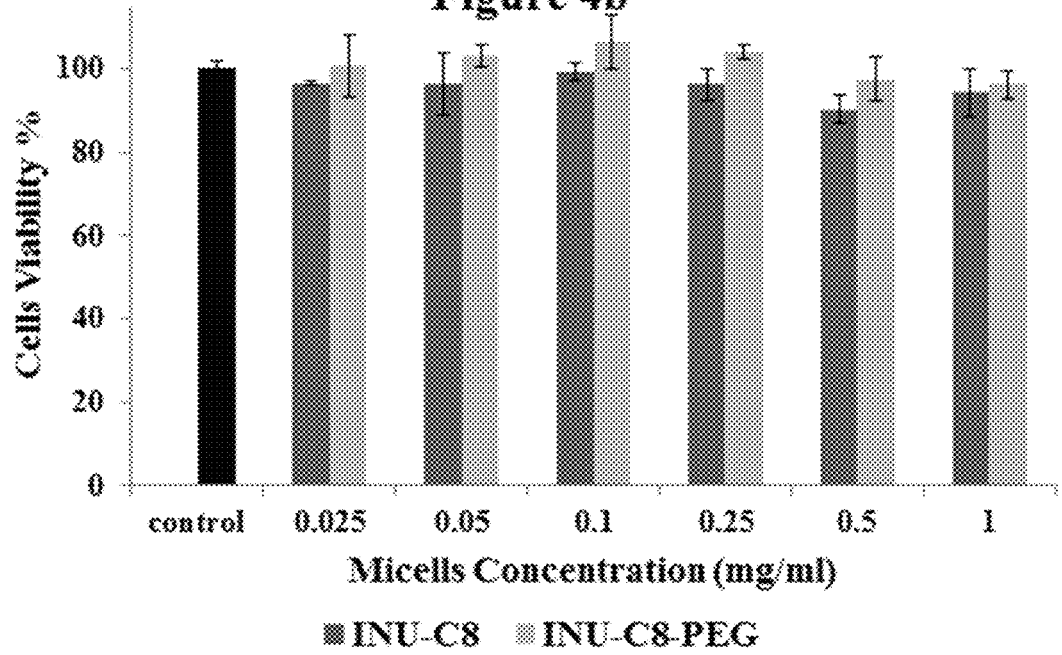

Figure 15
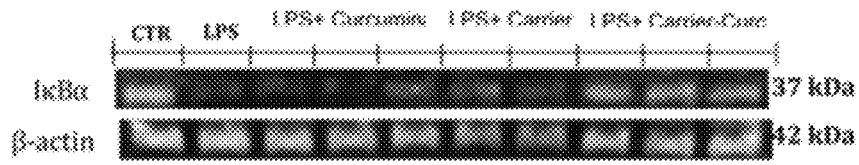
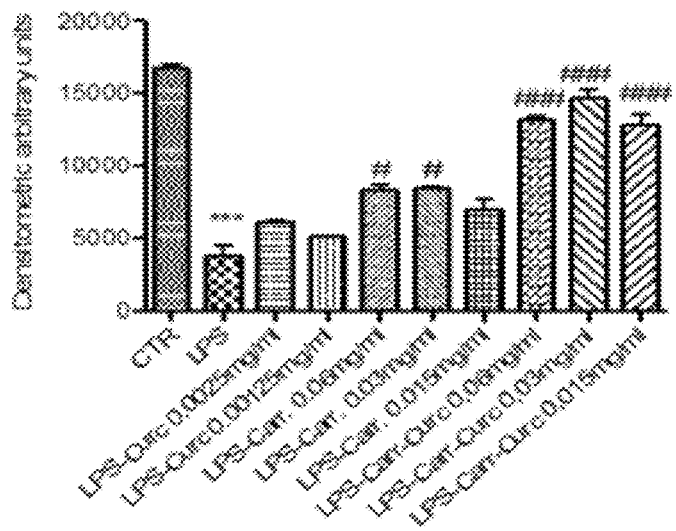
Figure 16
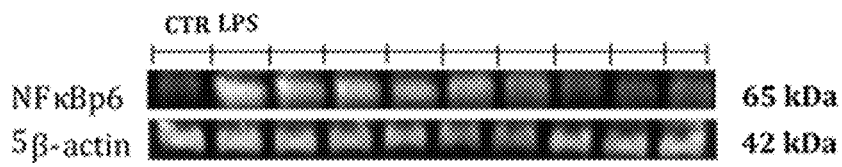
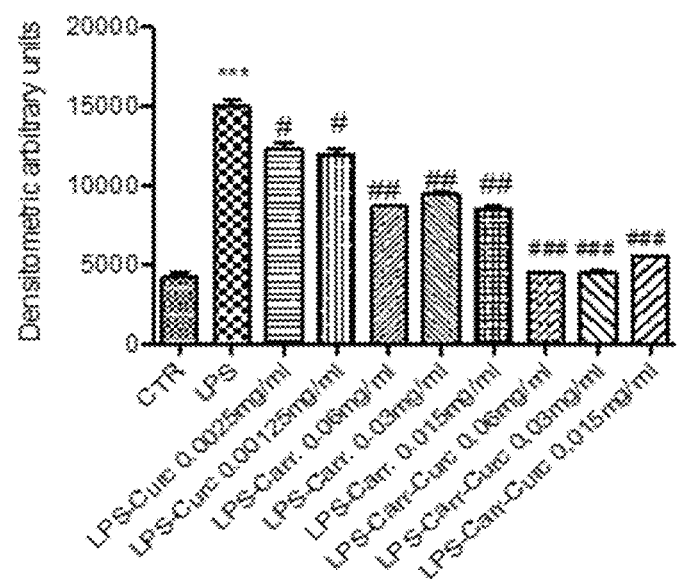

*** p<0,001 versus sham ; ## p< 0,01 versus LPS ; ### p< 0,001 versus LPS p< 0,01 versus LPS ; ### p< 0,001 versus LPS

NANOSTRUCTURED FORMULATIONS FOR THE DELIVERY OF SILIBININ AND OTHER ACTIVE INGREDIENTS FOR TREATING OCULAR DISEASES

This application is a divisional of prior filed U.S. application Ser. No. 15/517,018, filed Apr. 5, 2017, which is the U.S. National Stage of International Application No. PCT/IB2015/057732, filed Oct. 9, 2015, which designated the United States and has been published as International Publication No. WO 2016/055976A1 and which claims the priority to Italian Patent Application No. FI2014A000230, filed Oct. 9, 2014, the disclosures of which are incorporated in their entirety by reference herein, and made a part of this application.

FIELD OF THE INVENTION

The present invention relates to the field of products for the treatment of ocular diseases and to formulations containing the same.

PRIOR ART

Uncontrolled neoangiogenesis is implicated in the etiology of various diseases such as: solid tumors, rheumatoid arthritis, psoriasis and, at the ocular level, corneal neovascularization, age-related macular degeneration (ARMD or AMD), macular edema, retinopathy of prematurity (ROP), choroidal neovascularization (CNV), diabetic retinopathy (DR) and neovascular glaucoma.

AMD, like many other chronic diseases related to ageing, has a multifactorial origin and its onset is caused by an unfavorable combination of genetic and lifestyle-related factors.

Studies conducted on anti-VEGF (originally developed for cancer therapy) in the treatment of CNV led to use of pegaptanib (Macugen®, Pfizer) and ranibizumab (Lucentis®, Genentech) in the treatment of CNV. Bevacizumab (Avastin®, Genentech) is also currently used "off label" in the treatment of AMD.

It should also be considered that the treatment of AMD is not only limited to the treatment of choroidal neovascularization (intravitreal injections of anti-VEGF and photodynamic therapy), but also includes the use of a number of substances with antioxidant, anti-inflammatory and neuroprotective action capable of acting at different levels of the process leading up to the full-blown disease and acting to prevent the onset of the disease, slow its progression to advanced forms, reduce the tissue damage and enhance the action of anti-VEGF drugs.

Diabetic retinopathy (DR) is one of the most serious and frequent microvascular complications of type 1 and type 2 diabetes mellitus, which significantly affects the patient's quality of life as it often leads to blindness, due to the onset of macular edema and secondary retinal vitreous neovascularization.

The therapies for DR currently available aim at contrasting the angiogenic and inflammatory processes of retinal diseases and as a result, in some cases, they slow the progression of the disease.

Glaucoma is an optic neuropathy leading to the progressive loss of optic nerve tissue, leaving the head thereof exposed resulting in the loss of vision. Uveitis is an inflammation of part or all of the tunica media (vascular) of the eye consisting of iris, ciliary body and choroid.

The therapeutic tools currently available for treating posterior uveitis are intravitreal injections or implants (Taylor S. R. Et al, New developments in corticosteroid therapy for uveitis, Ophthalmologica. 2010; 224 Suppl 1:46-53), not without very important secondary effects (endophthalmitis, retinal edema, etc.) at the expense of the visual organ.

Over the last two decades, intravitreal injections have been considered very valuable because, compared to other administration routes, typically allow reaching higher concentrations in the retina and vitreous. Nevertheless, the intravitreous route is associated to serious risks for the patient, such as retinal detachment, endophthalmitis and intravitreal hemorrhages. Moreover, this administration route requires repeated injections of the drug to ensure the therapeutic effect, which often is not well tolerated by the patient.

Therefore, the treatments currently available are unsatisfactory because of the existing disproportion in the benefits/side effects ratio.

For this reason, non-biodegradable controlled release systems implantable in the vitreous (Vitrasert®, Retisert®) have been developed, but even these have the same risks associated with intravitreal injections, as well as the need for surgery for the implant and the possibility of rejection.

A compromise between risks and benefits was obtained using the periocular administration routes (peribulb, posterior juxtascleral, retrobulbar subtenon and subconjunctival), which are safer although less efficient than the intravitreal.

These routes of administration exploit the use of traditional injectable formulations and allow the active ingredient to reach the target site (the vitreous and the retina) by diffusion through the scleral fibrous tissue, which forms a barrier less resistant to drugs. The injected drug is in any case cleared through the front (outflow of the aqueous humor) or rear (retina and systemic circulation) path, requiring multiple administrations associated with poor patient compliance (pain, cataracts, retinal detachment, endophthalmitis and vitreous hemorrhages).

Currently, therefore, the treatment of diseases of the posterior segment of the eye has only drug delivery systems associated with undesired effects.

It is also known that the advanced drug delivery systems of the nanoparticle type today are the forefront of drug delivery.

Nanoparticle systems of a lipid nature such as solid lipid nanoparticles (SLN) and nanostructured lipid systems (NLC) are colloidal systems consisting of biocompatible lipids (pure triglycerides, complex mixtures of glycerides, waxes) and stabilized with non-toxic surfactants such as lecithins and poloxamers. They are between 100 and 500 nm in size. At room temperature, the particles are in the solid state.

It has already been shown that lipid nanoparticles increase the bioavailability of several drugs in the eye due to an increased pre-ocular retention time compared to the conventional pharmaceutical form, thus avoiding the repeated and frequent instillation (*Int. J. Pharm.*, 238 241-245 (2002)).

Inulin is a natural polysaccharide extractable from various plants and fruits. It is a carbohydrate consisting of linear chains of D-fructose units bound through β-1) gluco-furanoside bonds which occasionally binds a glucose molecule at its reducing end. Inulin, due to the fact that it has many advantageous properties (absence of toxicity, biocompatibility, solubility in water and probiotic effect on intestinal bacterial flora), is used in countless applications (Kolida S, Gibson G R. *J Nutr* 2007; 137:2503S-2506S; Gocheva et al., Colloids and Surfaces A: Physicochem. Eng. Aspects 2011; 391:101-104), and among them many in the biomedical field.

Recently, in order to get new drug delivery systems (DDS), such as hydrogels, nanoparticles, macromolecular bioconjugates and polymeric micelles, numerous researchers have focused their attention on the chemical modification of inulin.

This was chemically modified in the side-chain with primary amines, which have been used to obtain the conjugation with hydrophilic chains, such as polyethylene glycol (PEG), and with hydrophobic molecules such as ceramide.

Calixarenes are cyclic polyphenols easy to synthesize, even at low cost, which are characterized by remarkable synthetic versatility, a predisposition toward their functionalization at different levels and finally, a low degree of cytotoxicity and immunogenicity.

In recent years, calix[4]arenes have been intensely investigated as new molecular platforms for biomedical applications, supported by low cytotoxicity (Int. J. Pharm. 2004, 273, 57) and immunogenicity (Bioconjugate Chem. 1999, 10, 613) shown by their derivatives both in vitro and in vivo.

The suitable functionalization of the calixarene backbone has provided derivatives with anti-inflammatory, antitumor, antimicrobial and vaccine-mimic activity (Curr. Drug Discov. Technol. 2009, 6, 306; Chem. Soc. Rev. 2013, 42, 366, US 2010/0056482; WO2005123660 A2).

Water-soluble calixarenes similar to cyclodextrins for the capacity of complexing a drug within their hydrophobic cavity have been proposed as excipients for the pharmaceutical industry, while amphiphilic calixarenes capable of assembling in nanostructured systems in an aqueous medium are promising drug delivery systems (J. Sci. Ind. Res. 2012, 71, 21; Chem. Soc. Rev. 2013, 42, 366, EP 1 293 248 A1; US 2010/0185022 A19). Some of them have been properly engineered to release the drug according to external stimuli such as changes in the oxidation-reduction potential, temperature (ACSNANO, 2011, 5, 2880), pH (Phys. Rev. E, 2007, 73, 051904), enzymatic activity (RSC Advances, 2013, 3, 8058), etc. The ability of calixarene derivatives to penetrate the cell membrane (Chem. Commun. 2012, 48, 1129; J. Am. Chem. Soc. 2008, 130, 2892) and the ability to functionalize the calixarene backbone with homing groups that recognize and bind to complementary receptors present on the surface of the target cell, make calixarenes also promising systems for targeted drug delivery (Org. Biomol. Chem. 2015, 13, 3298).

Silibinin is a mixture of two diastereoisomers A and B in a proportion of about 1:1 contained in *Silybum marianum*.

Its main applications in the clinical field are: treatment of liver diseases caused by alcohol, hepatic cirrhosis, Amanitapoisoning, viral hepatitis, and drug-induced liver diseases.

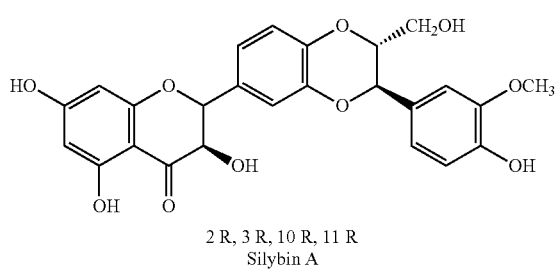

2 R, 3 R, 10 R, 11 R
Silybin A

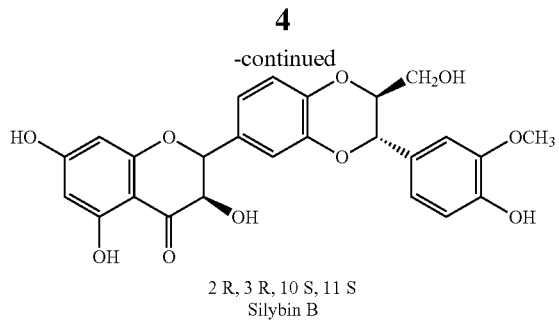

2 R, 3 R, 10 S, 11 S
Silybin B

On the other hand, it is known that the bioavailability and efficacy of silibinin is rather limited due to its low solubility in water (430 mg/L).

Silibinin seems to be an effective agent for the prevention and treatment of malignant gliomas in humans (Rana P. Singh, Oncogene, 2005).

Moreover, the antiangiogenic activity of silibinin particularly on AMD has been shown in vitro and after oral administration of a silymarin-based preparation.

In light of the above, the prospect of having new pharmacological formulations that may facilitate the physician in the therapeutic treatment of eye diseases, in particular neurodegenerative diseases, such as macular degeneration and diabetic retinopathy, increases the interest towards compounds such as silibinin functionalized to improve the in situ availability thereof.

In addition to silibinin extensively studied with all the nanostructured systems described, other active ingredients of natural origin and not characterized by low water solubility, easy chemical and enzymatic degradation, low bioavailability were investigated with some of these nanostructured formulations, such as: sorafenib, curcumin, latanoprost.

Sorafenib (BAY43-9006, Bayer)

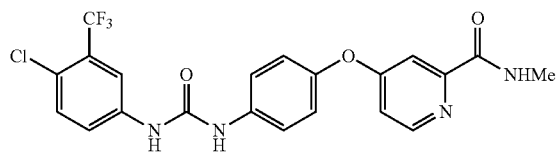 [SMILES: CNC(=O)c1cc(Oc2ccc(NC(=O)Nc3ccc(Cl)c(C(F)(F)F)c3)cc2)ccn1]

is a diaryl urea that acts on multiple targets (VEGF, PDGF, EGF; it is in fact defined as a multi-kinase inhibitor) with prevalent anti-VEGF action, provided with proven anti-angiogenic action in tumors (EP 114084061, Bayer), and it is the first antitumor agent approved in Europe for the treatment of hepatocellular carcinoma (Nexavar® tablets).

The therapeutic index of Sorafenib in the therapy of retinal diseases can be increased by using the local administration, at the ocular level: in this way, the pharmacological effect can be obtained while limiting the occurrence of systemic side effects. Moreover, the local administration allows the use of limited doses compared to those required for having the same effect via systemic administration and thus a reduction in the costs of the finished product.

Curcumin

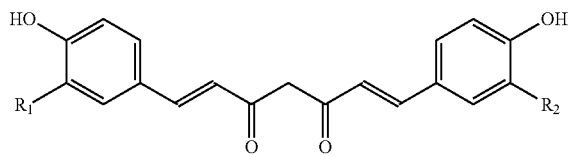

is a yellow polyphenol (diferuloylmethane) extracted from the rhizome of Curcuma Longa, an Asian plant used both in the culinary industry and in medicine for its curative properties in biliary diseases and in some inflammatory conditions.

Latanoprost

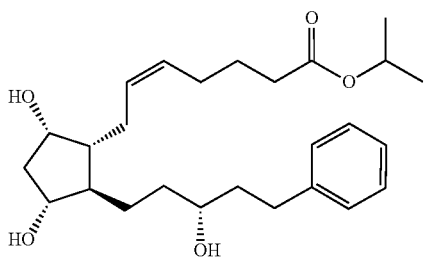 [SMILES: CC(C)OC(=O)CCC/C=C\C[C@@H]1[C@@H](CC[C@@H](O)CCc2ccccc2)[C@H](O)C[C@@H]1O]

is an active ingredient which like bimatoprost and travoprost is part of the prostaglandin analogs. Prostaglandin analogs are a class of drugs for topical use that has recently been used in the treatment of open-angle glaucoma; initially, they were not recommended as first-line treatment due to the lack of information about their long-term effects. Among the side effects associated with long-term treatment with prostaglandins, the major ones concern changes in the iris pigmentation, thickening and lengthening of eyelashes, onset of macular edema (Alexander C L et al., Prostaglandin analog treatment of glaucoma and ocular hypertension; Ann Pharmacother., 2002).

BRIEF DESCRIPTION OF THE FIGURES

FIG. 4 (a and b) shows the cytocompatibility profile of empty micelles of INU-C8 and INU-C8-PEG on the 16HBE cell line after 4 hours (4 a) and 24 hours (4 b) incubation at different concentrations.

FIG. 15 shows the reduction in the degradation of the constituent protein IkBα in J744 macrophages subjected to stress from LPS in the presence of curcumin, with curcumin, calixarene system and calixarene-curcumin system.

FIG. 16 shows the reduction of NFkB in J744 macrophages subjected to stress from LPS in the presence of curcumin, calixarene 1 and calixarene-curcumin.

SUMMARY OF THE INVENTION

Figure 1:
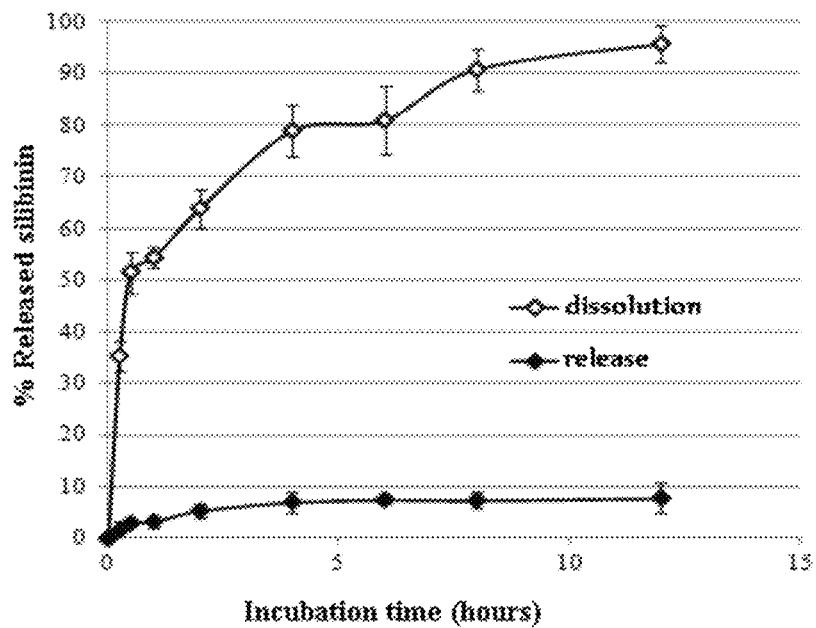
FIG. 1 shows the percentage of silibinin released by SLN-A in PBS at pH 7.4 as a function of the incubation time, compared to the dissolution curve of free silibinin.

Formulations for topical administration are described, containing silibinin incorporated in SLN and NLC lipid nanoparticle systems, and based on calixarenes, possibly mucoadhesive, or in micellar and nanoparticle systems based on amphiphilic inulin copolymers for use in the treatment of neurodegenerative ocular diseases.

DETAILED DESCRIPTION OF THE INVENTION

The present invention overcomes the drawbacks described above with formulations for topical application containing silibinin incorporated in:

(1) lipid nanoparticle systems of the SLN (Solid Lipid Nanoparticles) and NLC (Nanostructured Lipid Carriers) type;

(2) calixarene-based nanostructured systems;

(3) micellar and nanoparticle systems based on amphiphilic inulin copolymers, examples of incorporation and release of other active ingredients that have a use rationale for the ocular diseases of interest are provided for the latter.

Said formulations are capable of delivering the active ingredient up to the vitreous or to the retina in therapeutically effective doses for the treatment of neurodegenerative ocular diseases such as macular degeneration, diabetic retinopathy, glaucoma. The present invention further relates to the processes of preparation of the nanoparticle systems incorporating silibinin as defined above.

In particular, a general procedure described hereinafter was followed for the preparation of SLN and NLC type systems.

The lipid phase (consisting of a solid lipid or a mixture of a liquid lipid with a solid one) is molten to about 5-10° C. above its melting point.

Silibinin is solubilized in an aliquot of ethanol and then added to the molten lipid mixture under magnetic stirring.

The hot lipid mixture containing silibinin is then precipitated in an aqueous solution containing water, a surfactant or a mixture of surfactants (precipitation method), or emulsified with an aqueous solution containing water, a surfactant or a mixture of surfactants, previously heated at the same temperature. In the latter case, the resulting pre-emulsion is either: dispersed in water or an aqueous medium cooled at a temperature of between 2 and 5° C. (microemulsion method), or subjected to high pressure homogenization (high pressure hot homogenization method). In all cases, the resulting nano-emulsion is allowed to cool to room temperature to then be purified through exhaustive dialysis (COMW 12000-14000) against distilled water. Thereafter, the cryoprotectant is added to the nanoparticle dispersion, which can be subjected to centrifugation (4000 rpm for 10 min at 10° C.). Finally, after freeze-drying, the solid lipid nanoparticles are retrieved and stored in freezer for later characterization and/or coated with the mucoadhesive polymers. In the latter case, the INU-EDA and INU-DETA polymers and chitosan, in 0.1% aqueous solution, are added to the nanoparticle suspensions and incubated for 30 min at room temperature and under magnetic stirring.

The above lipid phase consists of lipids, for example selected from: triglycerides, such as tristearin, tripalmitin, caprylic/capric acid triglycerides (Mygliol); diglycerides such as Precirol ATO 5 (glyceryl distearate); monoglycerides such as glyceryl monosterate; aliphatic alcohols, such as cetyl alcohol; fatty acids (C10-C22); fatty acid esters with fatty alcohols, such as cetyl palmitate; mixtures of mono-, di- and triglycerides of pegylated and non-behenic acid such as Compritol HD-5-ATO (PEG-8 behenate and tribehenin) and Compritol 888ATO (mixture of mono-, di- and tribehenate); mono-, di- and triglycerides of pegylated caprylic and caproic acid such as Accocon CC-6.

The substances used as surfactants/co-surfactants in the process can be for example selected from: non-ionic surfactants including lecithins such as Epikuron 200; polyethylene glycol and polypropylene glycol block copolymers such as Pluronic; pegylated sorbitan derivatives, such as Tween; fatty alcohol ethers with polyethylene glycol such as Brij; ionic surfactants including bile salts such as sodium taurocholate; quaternary amines including cetylpyridinium chloride and bromide dioctadecyl dimethyl ammonium.

The substances used as cryoprotectants in the process can for example be selected from: sugars such as lactose and trehalose; polymers such as polyvinylpyrrolidone (PVP).

The substances used to impart mucoadhesion in the process are for example selected from: inulin polymers bearing amine groups (INU-EDA and INU-DETA), low molecular weight polymers (Chitosan) and cationic surfactants (CCP and DDAB).

According to a further embodiment, the invention relates to formulations for ophthalmic use containing inulin-based copolymers of the following formula (I) or (II), wherein R is $—(CH_2)_p—CH_3$; where p is in the range between 0 and 19;

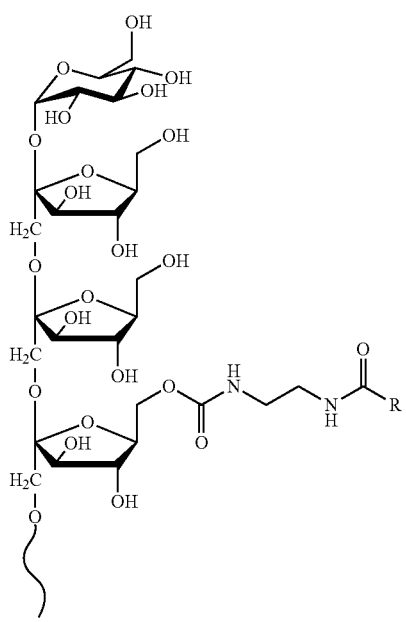

(I)

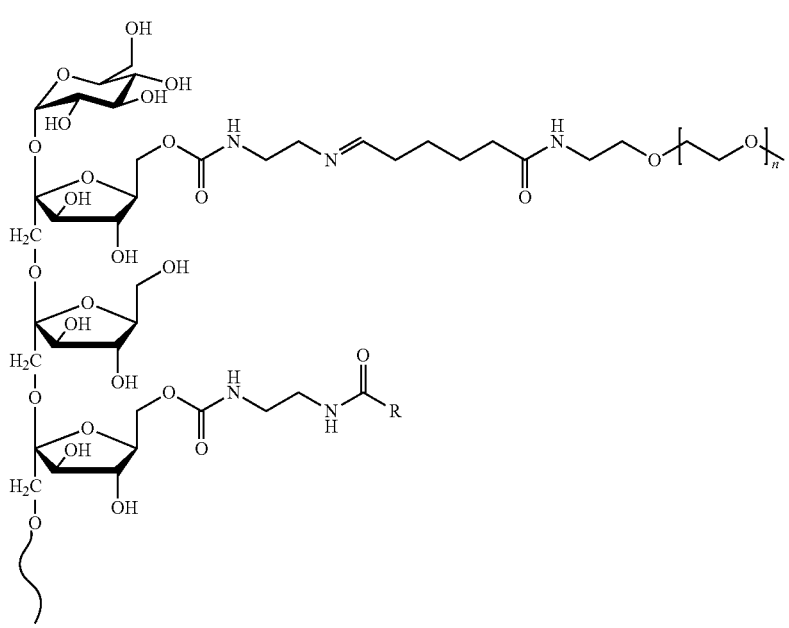

(II)

wherein R is —(CH$_2$)$_p$—CH$_3$; where p is in the range between 0 and 19 and n is in the range between 9 and 450 and to such copolymers.

The inulin-based copolymers of formula (I) and (II) as given above are obtained by functionalization of inulin with aliphatic chains C8 or with chains of C8 and PEG.

These copolymers, which have amphiphilic features, have proven to be able to aggregate to form micelles or nanoparticles, to incorporate flexible and different amounts of drug and release it into the active form for a prolonged and controlled time, moreover, they are highly biocompatible and allow easy making of the ophthalmic formulation.

The formulation is obtained by adding a certain amount of active ingredient such as sorafenib or silibinin to a polymer solution in DMF. The resulting solution is then dried under vacuum and dispersed in PBS at pH 7.4 by ultrasonication and stirring cycles (3 cycles of 10 minutes). Thereafter, the dispersion is placed in an orbital shaker for 18 hours at 25° C. and then dialyzed against water with a membrane having nominal cut-off (MWCO) of 1000 Da.

Finally, the resulting dispersion is freeze-dried.

According to a further embodiment of the present invention, it refers to formulations for ophthalmic use containing nanostructured systems based on amphiphilic calixarenes.

In such systems, the presence of multiple positively charged ligand units, in addition to imparting mucoadhesive properties, can facilitate the crossing of the corneal and retinal epithelium by the molecular recognition of complementary receptors present on the cell surface.

In particular, the present invention relates to formulations for topical ophthalmic use comprising cationic macromolecules consisting of calix[4]arene derivatives functionalized with alkoxyamines, including choline, to obtain new carriers of general formula (A)

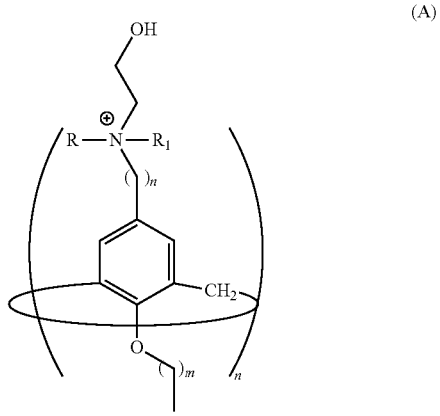

(A)

wherein:
R=CH3, (CH$_2$)$_x$CH$_3$, (CH$_2$)$_x$OH
R$_1$=CH3, (CH$_2$)$_x$CH$_3$, (CH$_2$)$_x$OH
Wherein
x=1-3
n=4, 6, 8
m=2-15
and wherein when R=R$_1$=CH$_3$ m is different from 2-9 which, in addition to delivering known active ingredients, are also provided with their own bioactivity which may potentiate that of the active ingredient.

As can be seen, formula A represents calixarene derivatives that differ in the number of phenolic units forming the macrocycle (n=4, 6, 8), in the length of the hydrophobic tails (m=2-15, indicates the number of CH2 groups), in the structure of the polar group present at the upper rim of calixarene (R and R1=CH3, (CH2)xCH3, (CH2)xOH, where x=1-3 and combinations thereof).

The calixarene compounds as described above are new and they are also an object of the present invention; these compounds have shown great versatility in charging and releasing active ingredients characterized by low water solubility, easy chemical and enzymatic degradation, low bioavailability, either of natural origin or not, to be used in the treatment of ocular diseases.

Choline as targeting molecule guides and promotes the crossing of the corneal epithelium, of the blood-retinal barrier and of the retinal epithelium (*Adv. Drug Deliv. Rev.* 2006, 58, 1136) where choline carriers are present.

Also in this case, as for the inulin-based copolymers described above, it was found that the calixarene systems have shown the ability to form nanoaggregates capable of incorporating and releasing silibinin or other active ingredients such as: curcumin/latanoprost.

Biocompatibility and ease of preparation characterize the formulation which is obtained by simple dissolution of the calixarene derivative in PBS (pH 7.4), addition of an excess of active ingredient (phase solubility method), sonication for 15 minutes, stirring at 25° C. for 2-3 days, centrifugation and filtration on GHP 0.2 µm filter.

The nanoparticle systems obtained in the present invention have an average diameter in the range between 50 and 200 nm with a polydispersity index below 0.5. A pharmacologically effective amount of active ingredient is incorporated in the described nanoparticles. In particular, the nanoparticle systems obtained in the present invention have a Drug Loading in the range between 1 and 15% w/w.

Further features and advantages of the present invention will appear more clearly from the following description of some embodiments thereof, made by way of non-limiting example.

The formulations according to the present invention containing an active ingredient selected from: silibinin or sorafenib or curcumin or latanoprost in lipid nanoparticle systems of the SLN (Solid Lipid Nanoparticles) and NLC (Nanostructured Lipid Carriers) type, or in nanostructured systems based on calixarenes, either mucoadhesive or not, or in micellar and nanoparticle systems based on amphiphilic inulin copolymers, allow the topical administration of the active ingredients for the treatment of neurodegenerative ocular diseases such as: CNV, AMD, macular edema, neovascular glaucoma, macular edema, retinopathy of prematurity (ROP), diabetic retinopathy (DR), uveitis, endophthalmitis, retinitis, choroiditis, chorioretinitis, retinal complications of systemic diseases.

The formulations are normally in the form of freeze-dried solid product and may contain, in addition to the active ingredient incorporated in the lipid, polymer or calixarene nanostructure as described above, also components such as surfactants and/or cryoprotectants and other excipients commonly used in ophthalmic preparations.

Example 1

Preparation of SLN Containing Silibinin (SLN-A)
The procedure and the experimental data obtained with the SLN object of the invention prepared with Compritol HD-5-ATO, loaded with silibinin, are described hereinafter.
Preparation of SLN-A The SLN-A were prepared with the high pressure hot homogenization method. Two hundred milligrams of Compritol HD5ATO were molten to about 5-10° C. above its melting point (65-70° C.). The drug (68 mg) was solubilized in an aliquot of ethanol (0.5 mL) and then added to the molten lipid mixture under magnetic stirring. The hot lipid mixture containing the drug was then emulsified in an aqueous solution of the Pluronic F68 surfactant (60 mg in 100 mL), previously heated at the same temperature. The resulting pre-emulsion is subjected to high pressure homogenization (4 cycles at 7500±2500 psi) using the Emulsiflex-C5 equipment (Avestin), placed in a hot water bath at a temperature of 65-70° C. The resulting nano-emulsion is allowed to cool to room temperature to then be purified by dialysis (COMW 12000-14000) against distilled water. Thereafter, the cryoprotectant trehalose (lipids:cryoprotectant weight ratio=1:1 w/w) is added to the nanoparticle dispersion, which was subjected to centrifugation (4000 rpm for 10 min at 10° C.). Finally, after freeze-drying using a Modulyo freeze-dryer, the SLN are retrieved and stored in freezer for subsequent characterization.

Size Determination and Zeta Potential Measurement of SLN-A Systems

The average diameter and the polydispersity index (PDI) of the SLN-A systems prepared were determined by photocorrelation spectroscopy (PCS) using a Zetasizer Nano ZSP (Malvern Instrument). Each sample was suitably diluted for the analysis with an aqueous solution of NaCl 0.9% w/w, filtered through 0.2-µm filters and the reading was made at an angle of 173° relative to the incident ray and analyzed in triplicate.

The zeta potential was measured according to the principles of the laser doppler velocimetry and of the light scattering analysis (M3-PALS technique) using a Zetasizer Nano ZSP (Malvern) with a He—Ne laser, power=4.0 mW, wavelength=633 nm. The results obtained for average diameter, PDI and zeta potential are given in Table 1.

TABLE 1

Average hydrodynamic diameter, polydispersity index (PDI), zeta potential of SLN-A systems.
DLS (in NaCl 0.9% w/w)

|  | Z-average (nm) | PDI | Potential $\zeta$ (mV ± SD) |
|---|---|---|---|
| PRE-freeze drying | 189.0 | 0.22 | −9.4 ± 1.2 |
| POST-freeze drying | 171.5 | 0.31 | −6.5 ± 3.5 |

Determination of Drug Loading (% DL) of SLN-A

In order to determine the amount of silibinin loaded in the SLN-A sample, 10 mg of the composition previously subjected to freeze-drying were solubilized in tetrahydrofuran (THF). The organic solution was then treated with methanol to precipitate lipids and extract the active ingredient. The resulting suspension was then filtered through 0.45 µm filters and analyzed by HPLC. The results obtained in terms of % DL (expressed as a percentage of the active ingredient loaded into the SLN, considering 100 mg of the material subjected to freeze-drying, consisting of lipids+active ingredient) was found to be 8.5% w/w.

Releases at pH 7.4 of Silibinin From SLN-A

The system described in the present invention was subjected to release studies in vitro at 37° C. using a phosphate buffer at pH 7.4 with incubation times in the range between 0 and 12 hours. The results obtained have shown that the system of the present invention slowly releases the drug up to a maximum of 7.8% w/w within 12 hours. The release and dissolution profiles of the drug after incubation at pH 7.4 and at 37° C. are shown in FIG. 1.

The system described is stable, i.e. it releases the drug very slowly into the external medium at pH 7.4 and this can be advantageous in order to optimize the delivery of the active ingredient in the pathological site by the nanoparticle containing it.

Example 2

Preparation of NLC Containing Silibinin (NLC-B)

By way of non-limiting example, the procedure and the experimental data obtained with the NLC object of the invention prepared with Compritol HD-5-ATO, Gelucire 44/14 and Acconon CC-6, loaded with silibinin, are described hereinafter.

Preparation of NLC-B

The NLC-B were prepared with the solvent precipitation-evaporation method. Compritol HD5ATO (250 mg) was molten to about 5-10° C. above its melting point (65-70° C.) and the drug (30 mg) was added to the molten lipid. Gelucire 44/14 (100 mg) and Acconon CC-6 (100 mg) were solubilized in ethanol (2.0 mL) and then added to the molten lipid mixture under magnetic stirring. The hot lipid mixture containing the drug and the surfactants was then precipitated in a hot aqueous solution containing surfactant sodium taurocholate (100 mg in 100 mL), previously heated at the same temperature and subjected to homogenization using Ultra-Turrax (13.500 rpm). The hot nanoparticle suspension, still under stirring, is placed in an ice bath until its temperature reaches the value of 10° C. The resulting nanoparticles are then purified by dialysis (COMW 12000-14000) against distilled water for 3 days and then the cryoprotectant trehalose is added (lipid:cryoprotectant weight ratio=1:2 w/w). Finally, after freeze-drying using a Modulyo freeze-dryer, the NLC are retrieved and stored in freezer for subsequent coating with an inulin derivative (INU-DETA) and chitosan. In the case of coating with INU-DETA, 9 mL of dyalized nanoparticle suspension (conc. of 4.3 mg/mL) were incubated with 1 mL of 0.1% INU-DETA for 1 h under magnetic stirring. In the case of coating with low molecular weight (5000 Mw) chitosan, 9 mL of dyalized and freeze-dried nanoparticles (conc. of 0.165 mg/mL) with addition of trehalose were incubated with 1 mL of 0.1% Chitosan for 30 min under magnetic stirring. The coated nanoparticles were then freeze-dried and stored as a powder for subsequent characterization.

Size Determination and Zeta Potential Measurement of NLC-B Systems

The average diameter and the polydispersity index (PDI) of the NLC-B systems coated with INU-EDA and chitosan prepared were determined by photo-correlation spectroscopy (PCS) using a Zetasizer Nano ZSP (Malvern Instrument). Each sample was suitably diluted for the analysis with an aqueous solution of NaCl 0.9% w/w, filtered through 0.2-µm filters and the reading was made at an angle of 173° relative to the incident ray and analyzed in triplicate.

The zeta potential was measured according to the principles of the laser doppler velocimetry and of the light scattering analysis (M3-PALS technique) using a Zetasizer Nano ZSP (Malvern) with a He—Ne laser, power=4.0 mW, wavelength=633 nm. The results obtained for average diameter, PDI and zeta potential are given in Table 2.

TABLE 2

Average hydrodynamic diameter, polydispersity index (PDI), zeta potential of NLC-B coated with INU-DETA and chitosan.
DLS (in NaCl 0.9%)

|  | Z-average (nm) | PDI | Potential $\zeta$ (mV ± SD) |
|---|---|---|---|
| NLC-B INU-DETA | 236.8 | 0.45 | −1.1 |
| NLC-B chitosan | 69.1 | 0.45 | +18.2 |

Determination of the % DL of the NLC-B Coated With INU-DETA and Chitosan

In order to determine the amount of silibinin loaded in the NLC-B samples coated with INU-DETA and chitosan, 2 mg of the compositions previously subjected to freeze-drying were hot-solubilized in 8 mL of ethanol (EtOH) and sonicated for 3 min. The resulting solutions were then filtered with 5.00 µm regenerated cellulose filters and analyzed with HPLC.

The results obtained in terms of % DL (expressed as a percentage of active ingredient loaded into the NLC, considering 100 mg of the material subjected to freeze-drying, consisting of lipids+active ingredient) were found to be 6.05% w/w for the NLC-B coated with INU-DETA and 3.07% w/w for the NLC-B coated with chitosan.

Figure 2:
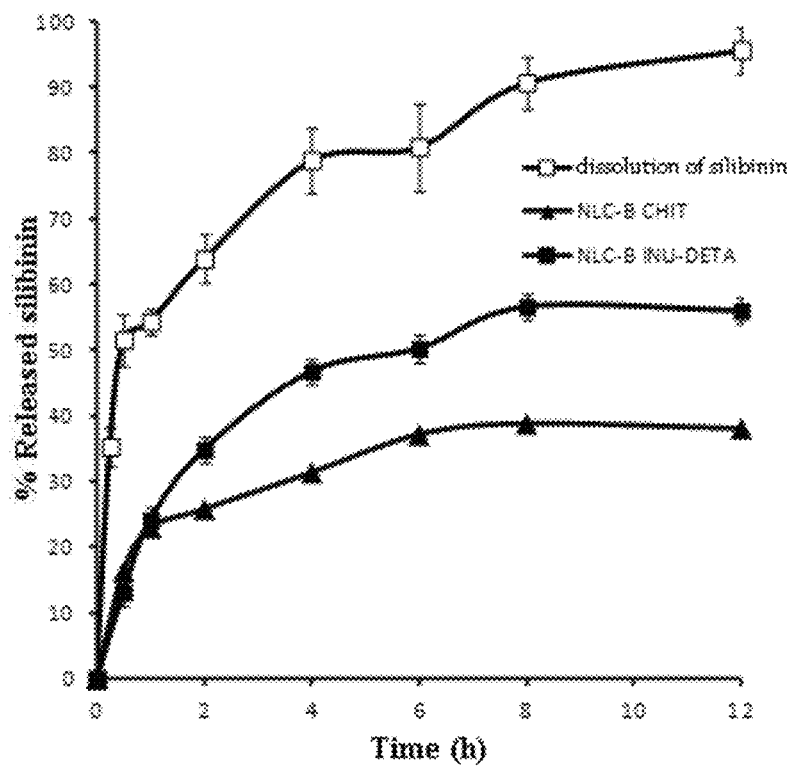
FIG. 2 shows the percentage of silibinin released by NLC-B systems coated with INU-DETA and chitosan in PBS at pH 7.4 as a function of the incubation time, and dissolution curve of free silibinin.

Releases at pH 7.4 of the Active Ingredients From NLC-B Coated With INU-DETA and Chitosan The NLC-B systems coated with INU-DETA and chitosan described in the present invention were subjected to release studies in vitro at 37° C. using a phosphate buffer at pH 7.4 with incubation times in the range between 0 and 12 hours. The results obtained have shown that both systems of the present invention slowly release the drug up to a maximum of 50% w/w within 12 hours for the NLC-B coated with INU-DETA and up to a maximum of 30% w/w within 12 hours for the NLC-B coated with chitosan. The release and dissolution profiles of the drug silibinin from the 2 coated systems after incubation at pH 7.4 and at 37° C. are shown in FIG. 2.

Preparation of Polymeric Micelles Based on INU-$C_8$ and INU-$C_8$-$PEG_{2000}$

By way of non-limiting example, the procedure and the experimental data obtained with polymeric micelles object of the invention based on INU-$C_8$ and INU-$C_8$-$PEG_{2000}$, loaded with silibinin or sorafenib, are described hereinafter.

Determination of the Critical Aggregation Concentration (CAC) of INU-$C_8$ and INU-$C_8$-$PEG_{2000}$ Copolymers The production of INU-$C_8$ and INU-$C_8$-$PEG_{2000}$ copolymers was carried out, with a good yield, following procedures already existing in the literature.

The CAC of INU-$C_8$ and INU-$C_8$-$PEG_{2000}$ copolymers was determined by spectrofluorimetric analysis, using pyrene as fluorescent probe. 20 µL of a solution of pyrene in acetone ($6.0 \times 10^{-5}$M) were placed into vials and evaporated at 37° C. on an orbital shaker until dryness. Thereafter, 2 mL of an aqueous solution of copolymer at increasing concentration and in the range between $1 \times 10^{-5}$ and 5 mg/mL were added into the vials containing the pyrene residue so as to obtain a final concentration of pyrene equal to $6.0 \times 10^{-7}$M. The dispersion thus obtained were maintained at 37° C. for 24 hours under constant stirring in order to balance the probe with the micelles. The emission and excitation spectra of pyrene were recorded using the following wavelengths, respectively: 373 nm and 333 nm. The results are shown in Table 3.

TABLE 3

CAC of some prepared copolymers

| COPOLYMER | CAC (mg/mL) |
|---|---|
| INU-$C_8$ | 0.3 |
| INU-$C_8$-PEG | 1.2 |

Preparation of Polymeric Micelles of INU-C8 and INU-C8-PEG Loaded With Silibinin or Sorafenib The polymeric micelles loaded with silibinin and sorafenib were prepared through the dry complexation method (kneading). In detail, 200 mg of INU-C8 or INU-C8-PEG were dry mixed with the drug (50 mg) using a mortar and pestle and ground in the presence of ethanol (5 mL). Thereafter, the dry matrix formed by the polymer wherein the drug was dispersed evenly, obtained after evaporation of ethanol, was hydrated slowly and under mechanical stirring in order to promote the self-aggregation of unimers and the incorporation of the drug within the hydrophobic core of the resulting micelles.

The resulting dispersion was subjected to sonication and stirring cycles (3 cycles of 10 minutes). Thereafter, the dispersion was centrifuged at 2000 rpm for 5 minutes and filtered on syringe filters with 5 µm cut off to remove the drug not incorporated. Finally, the resulting dispersion was frozen in liquid nitrogen and freeze-dried.

Determination of the % DL of the Polymeric Micelles of INU-C8 and INU-$C_8$-$PEG_{2000}$ 3 mg of micelles loaded with silibinin or loaded with sorafenib were dispersed in methanol (5 mL); the dispersion was sonicated for 10 minutes and then left to stir vigorously for 4 hours. After this time, the dispersion was filtered using a syringe filter with 0.2 µm cut off, and finally the filters were washed with methanol (5 mL) to obtain a final volume of 10 mL. For the determination of silibinin at 600 µL of the solution in methanol obtained from the extraction procedure, 400 µL of 1% acetic acid (v/v) were added to comply with the composition of the eluent mixture used for the HPLC analysis. Therefore, the amount of drug extracted from the micelles was determined through HPLC analysis, using a C6-phenyl, methanol:acetic acid column at 1% (v/v) (60:40) as eluent phase. The flow rate was set to 0.65 mL/min and the eluate was monitored at 288 nm.

For the determination of sorafenib, 1 mL of the solution in methanol obtained from the extraction procedure was directly analyzed by HPLC in order to determine the amount of drug incorporated by the micelles. The HPLC analysis was performed using a C6-phenylmethanol:water (v/v) (90:10) column as eluent phase. The flow rate was set to 1 mL/min and the eluate was monitored at 266 nm.

The results are shown in Table 4. Determination of the average size and of the zeta potential of polymeric micelles of INU-C8 and INU-C8-PEG The size distribution of micelles was determined through dynamic light scattering measurements using the Malvern Zetasizer Nano ZS. These measurements were conducted at a fixed angle of 173° and at a temperature of 25° C. The aqueous solutions of micelles (2 mg/mL) were analyzed after filtration through cellulose membrane filters with 5 µm cut off. The average hydrodynamic diameter and the polydispersity index (PDI) were obtained using cumulative analyses of the correlation function. The zeta potential (mV) was calculated by the electrophoretic mobility and using the Smoluchowsky relation, assuming that K·a>>1 (where K and a are the Debye-Hückel parameter and the particle radius, respectively). The results are shown in Table 4. As can be seen, all the copolymers are able to incorporate the hydrophobic drug sorafenib and silibinin.

TABLE 4

Average hydrodynamic diameter, polydispersity index (PDI), zeta potential and drug loading of micelles.

| Micelles | Average diameter (nm) | DI | Zeta potential (mV) | Drug[a] loading (%) |
|---|---|---|---|---|
| INU-$C_8$-Silibinin | 164.9 | 0.27 | +21.9 ± 3.82 | 1.7 ± 0.5 |
| INU-$C_8$-PEG-Silibinin | 166.7 | 0.46 | +18.5 ± 3.5 | 1.8 ± 0.1 |
| INU-$C_8$-Sorafenib | 150.4 | 0.16 | +19.9 ± 4 | 18.45 |
| INU-$C_8$-PEG-Sorafenib | 179.7 | 0.18 | +26.5 ± 3.7 | 11.41 |

[a]The drug loading refers to sorafenib and silibinin

Release Studies

Figure 3:
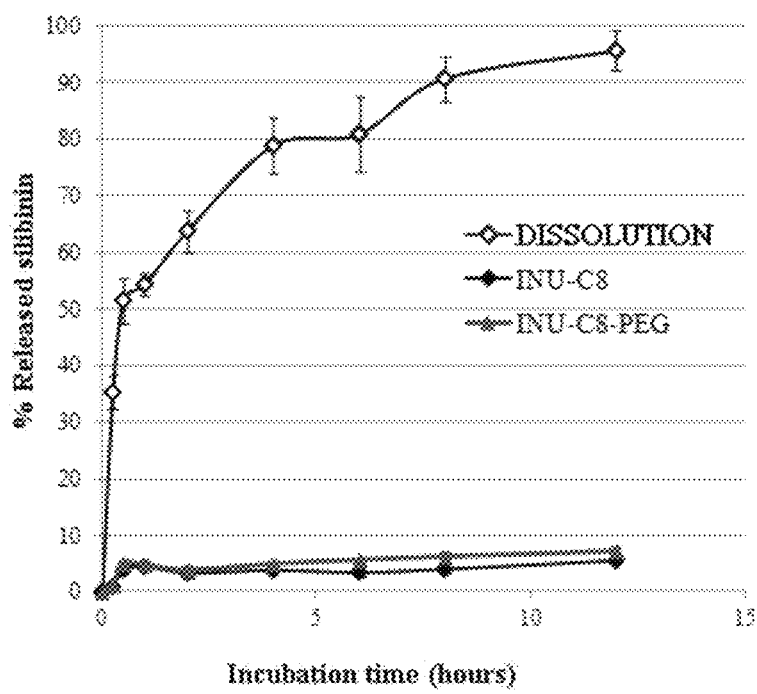
FIG. 3 shows the percentage of silibinin released by the polymeric micelles of INU-C8 and INU-C8-PEG in PBS at pH 7.4 as a function of the incubation time, compared to the diffusion curve of free silibinin.

In order to assess the ability of the systems obtained to release the incorporated drug, appropriate amounts of polymeric micelles of INU-C8 and INU-C8-PEG (15 mg) were dispersed in PBS, pH 7.4 (5 mL) and transferred in a floating dialysis membrane Spectra/Por with nominal cut off (MWCO) of 1 kDa. The dialysis membranes containing the micelle dispersions loaded with drug and the drug alone were immersed in PBS at pH 7.4 (50 mL) and incubated at 37° C. for 24 hours under continuous stirring (100 rpm) in a Benchtop 808C Orbital Shaker incubator model 420. At scheduled time intervals, aliquots of external medium (1 mL) were taken from outside the dialysis membrane and replaced with an equal amount of fresh medium. The samples taken were freeze-dried, suspended in methanol: acetic acid 1% (v/v) and analyzed by HPLC in order to determine the amount of drug released. By way of example, the release graph of the active ingredient silibinin incorporated in the systems is shown. All the release all data obtained were compared with the diffusion profile of silibinin alone (0.25 mg), obtained using the same procedure (FIG. 3). The data were corrected taking into account the dilution process. Each experiment was conducted in triplicate and the results were found to be in conformity with the standard error±5%. As can be seen from the graph, the polymeric micelles of INU-C8 and INU-C8-PEG loaded with silibinin show a very slow release kinetics compared to the diffusion of free silibinin (less than 5% w/w of silibinin is released after 12 h incubation). Similar release profiles were also obtained for the active ingredient sorafenib.

Stability Studies

The stability of micelles of INU-C8 and INU-C8-PEG loaded with silibinin or sorafenib was assessed by incubating the freshly freeze-dried systems for 1, 2 and 3 months at 4° C. and 25° C. In particular, the samples freshly prepared and freeze-dried were stored at a controlled temperature for 1, 2 and 3 months. After the incubation period, the samples were dispersed in bidistilled water (2 mg/mL) and analyzed by dynamic light scattering measurements in order to evaluate the average diameter, polydispersity index and zeta potential thereof. Separately, 3 mg of sample were dispersed in methanol (5 mL); the dispersion was first sonicated for 10 minutes and stirred for 2 h and finally, filtered through syringe filters with 5 µm cut off and diluted with additional 5 mL methanol. The amount of active ingredient extracted was determined through HPLC analysis, using the same procedure described for the determination of drug loading.

The results obtained show that both the micelles prepared and the drug loaded have good physical stability for long periods of storage. As an example, Table 5 shows the stability data related to INU-C8 micelles loaded with silibinin or sorafenib obtained through dynamic light scattering measurements in order to evaluate changes in the average diameter, in the PDI and in the zeta potential, and HPLC analysis to assess the drug loading and stability of the loaded drug.

TABLE 5

Stability of INU-C8 micelles loaded with silibinin/sorafenib, 1 and 2 after 3 months of storage at 4 and 25° C.

| Incubation time | Average diameter (nm) | PDI | Zeta potential (mV) | Drug loading (%) |
|---|---|---|---|---|
| INU-C$_8$ micelles | | | | |
| Time 0 | 164.9 | 0.27 | +21.9 ± 3.82 | 1.7 ± 0.5 |
| 1 month 4° C. | 153.3 | 0.37 | +10.9 ± 4.3 | 1.9 ± 0.9 |
| 1 month 25° C. | 188.2 | 0.26 | +10.9 ± 4.2 | 1.7 ± 0.9 |
| 2 month 4° C. | 195.8 | 0.39 | +7.38 ± 3.4 | 1.7 ± 0.3 |
| 2 month 25° C. | 185.6 | 0.44 | +6.37 ± 3.9 | 1.7 ± 0.7 |
| 3 month 4° C. | 137.8 | 0.32 | +8.76 ± 4.5 | 1.7 ± 0.3 |
| 3 month 25° C. | 151.6 | 0.38 | +7.88 ± 3.3 | 1.7 ± 0.7 |
| INU-C$_8$ Sorfenib micelles | | | | |
| Time 0 | 150.4 | 0.16 | +19.9 ± 4 | 18.4 ± 0.5 |
| 1 month 4° C. | 153.8 | 0.15 | +23.82 ± 4.72 | 19 ± 0.9 |
| 1 month 25° C. | 198.5 | 0.098 | +29.9 ± 5.39 | 17 ± 0.9 |
| 2 month 4° C. | 160.8 | 0.15 | +31.6 ± 5.46 | 17.5 ± 0.3 |
| 2 month 25° C. | 431.8 | 0.29 | −0.644 ± 3.33 | 18.3 ± 0.7 |
| 3 month 4° C. | 250.3 | 0.22 | +15.7 ± 5.5 | 18.1 ± 0.3 |
| 3 month 25° C. | 318 | 0.273 | +17.1 ± 3.4 | 17.3 ± 0.7 |

In Vitro Cytocompatibility Studies

The biocompatibility of empty micelles of INU-C8 and INU-C8-PEG was evaluated on the human bronchial epithelium (16HBE) cell line through MTS assay, using a commercial kit (Cell Titer 96 Aqueous One Solution Cell Proliferation assay, Promega). The cells were plated on 96 well plates with a density of $2 \cdot 10^4$ cells per well, and suspended in Dulbecco's modified eagle's medium (DMEM), enriched with 10% vol/vol of fetal bovine serum (FBS), 1% vol/vol of antibiotics (10 mg/mL streptomycin 10000 U-1 mL penicillin), and incubated under standard conditions (95% RH and 5% CO2 at 37° C.). After 24 hours of incubation, the medium was removed and replaced with 200 µL of fresh medium containing the empty micelles of INU-C8 and INU-C8-PEG at a concentration equal to 0.025, 0.05, 0.1, 0.25, 0.5 and 1 mg/mL. After 4 and 24 hours of incubation, the dispersion of micelles in DMEM was removed, the cells were washed 1 time with Dulbecco's Phosphate buffered saline (DPBS) and incubated for 2 hours at 37° C. with 100 µL of fresh medium and 20 µL of MTS solution. The cells incubated with DMEM alone were used as negative controls. The results were expressed as percentage reduction of the cell viability compared with control cells (FIGS. 4a and 4b). All experiments were conducted in triplicate.

The studies conducted show that the polymeric micelles tested have a good cytocompatibility and do not exhibit cytotoxic effects in vitro on the human bronchial epithelium cell line. This result makes these systems potentially usable as efficient systems for in vivo drug delivery. The biocompatibility of the empty systems and loaded with the active ingredients studied was also confirmed on ARPE-19 retinal cells and on SIRC corneal epithelial cells.

Figure 5:
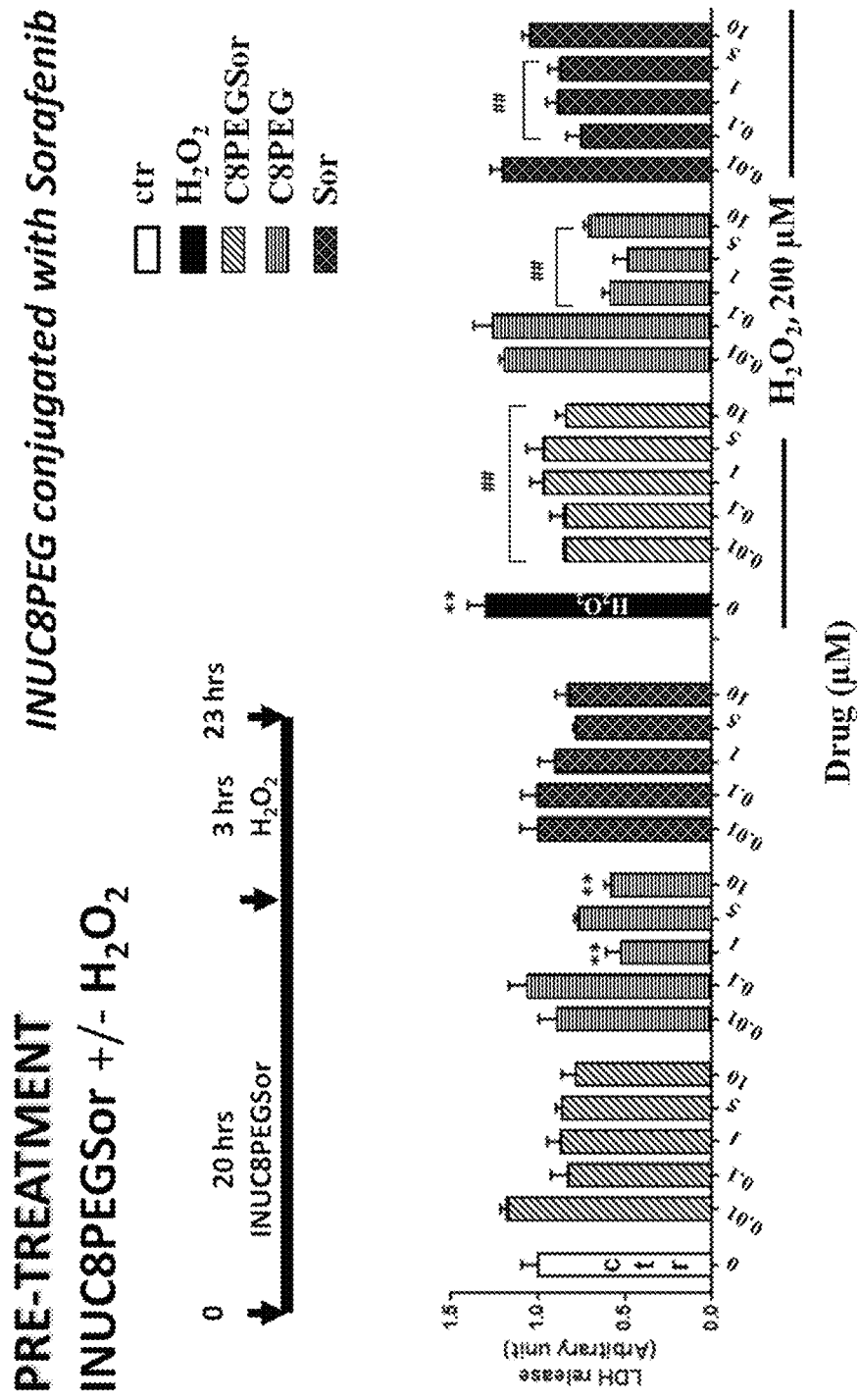
FIG. 5A shows the effect on ARPE-19 cells pretreated for 20 hours with the INUC8PEG-Sorafenib system, with the empty carrier INUC8PEG and with Sorafenib tosylate, thereafter, they were exposed to insult with $H_2O_2$; quantification of LDH release into the medium.
FIG. 5B shows the effect on ARPE-19 cells insulted with $H_2O_2$ for three hours and post-treated for 20 hours with the INUC8PEG-Sorafenib system (C8PEGSor), with the empty carrier INUC8PEG (C8PEG) and with Sorafenib tosylate (Sor); quantification of LDH release into the medium.
Figure 5:
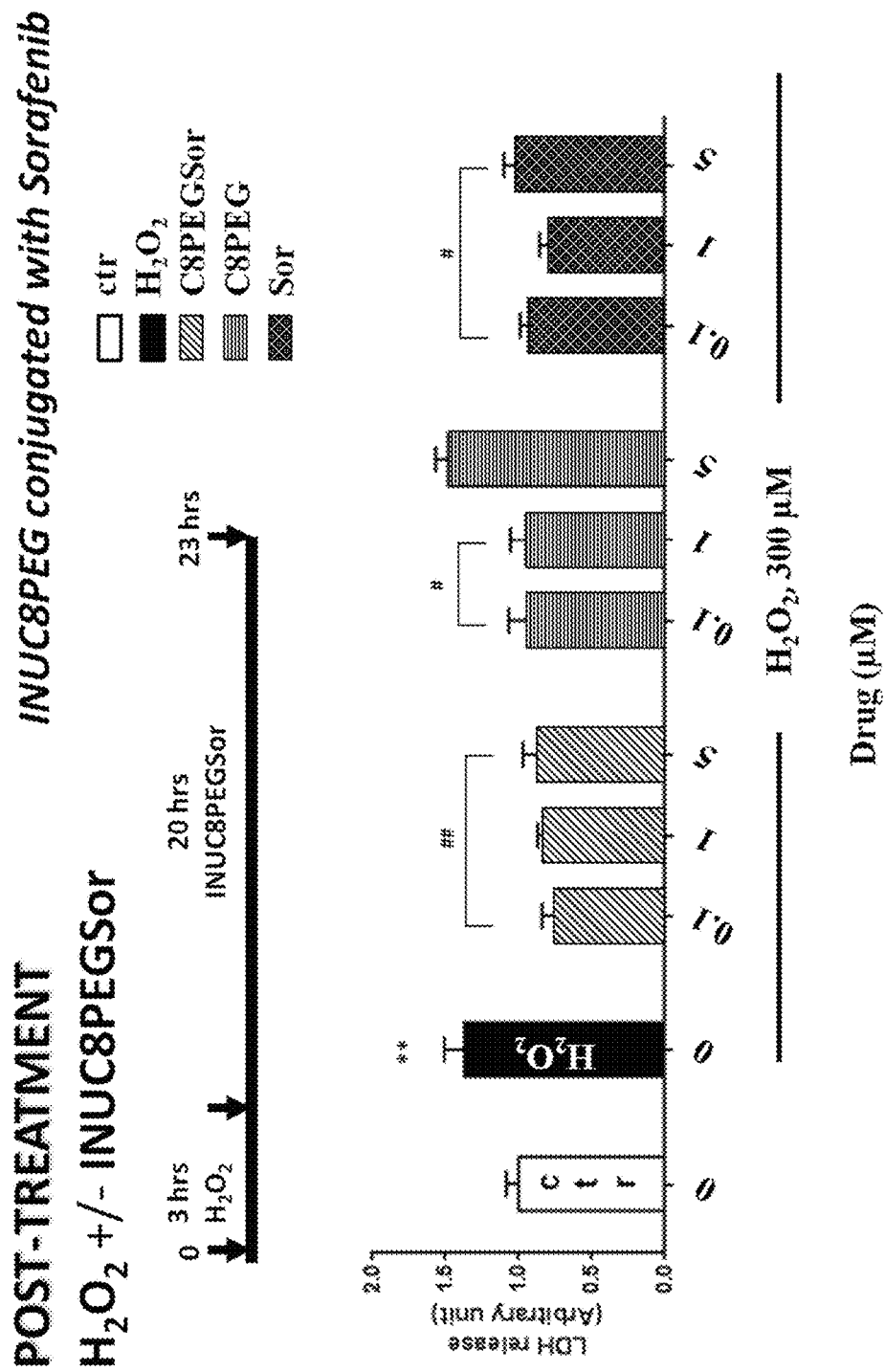
Figure 6:
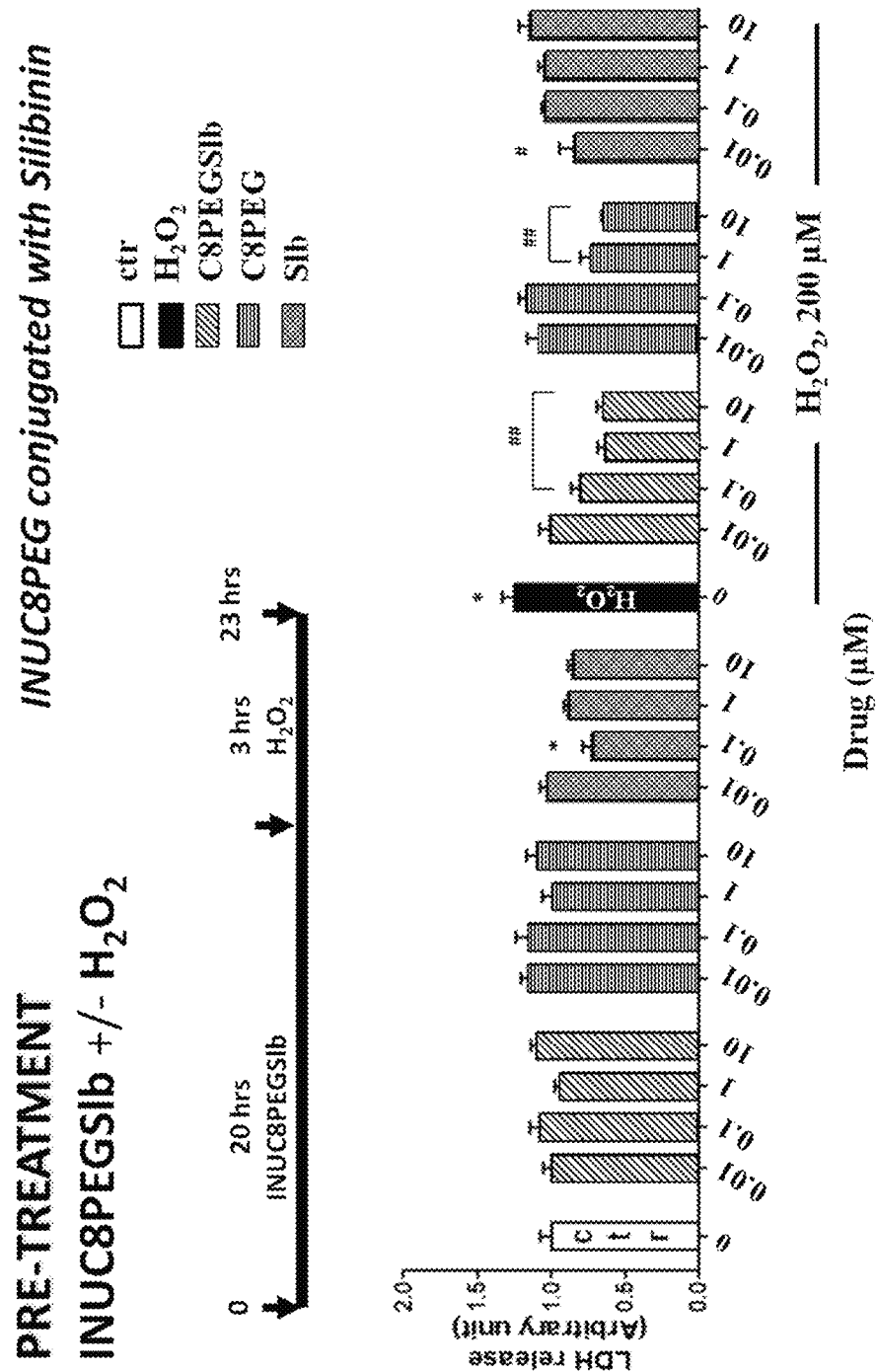
FIG. 6A shows the effect on ARPE-19 retinal cells pretreated for 20 hours with the INUC8PEG-Sorafenib system, with the empty carrier INUC8PEG and with silibinin, then exposed to insult with $H_2O_2$; quantification of LDH release into the medium.
FIG. 6B shows the effect on ARPE-19 retinal cells insulted with $H_2O_2$ for three hours and post-treated for 20 hours with the INUC8PEG-silibinin system (C8PEGSib), with the empty carrier INUC8PEG (C8PEG) and with silibinin (Sib); quantification of LDH release into the medium.
Figure 6:
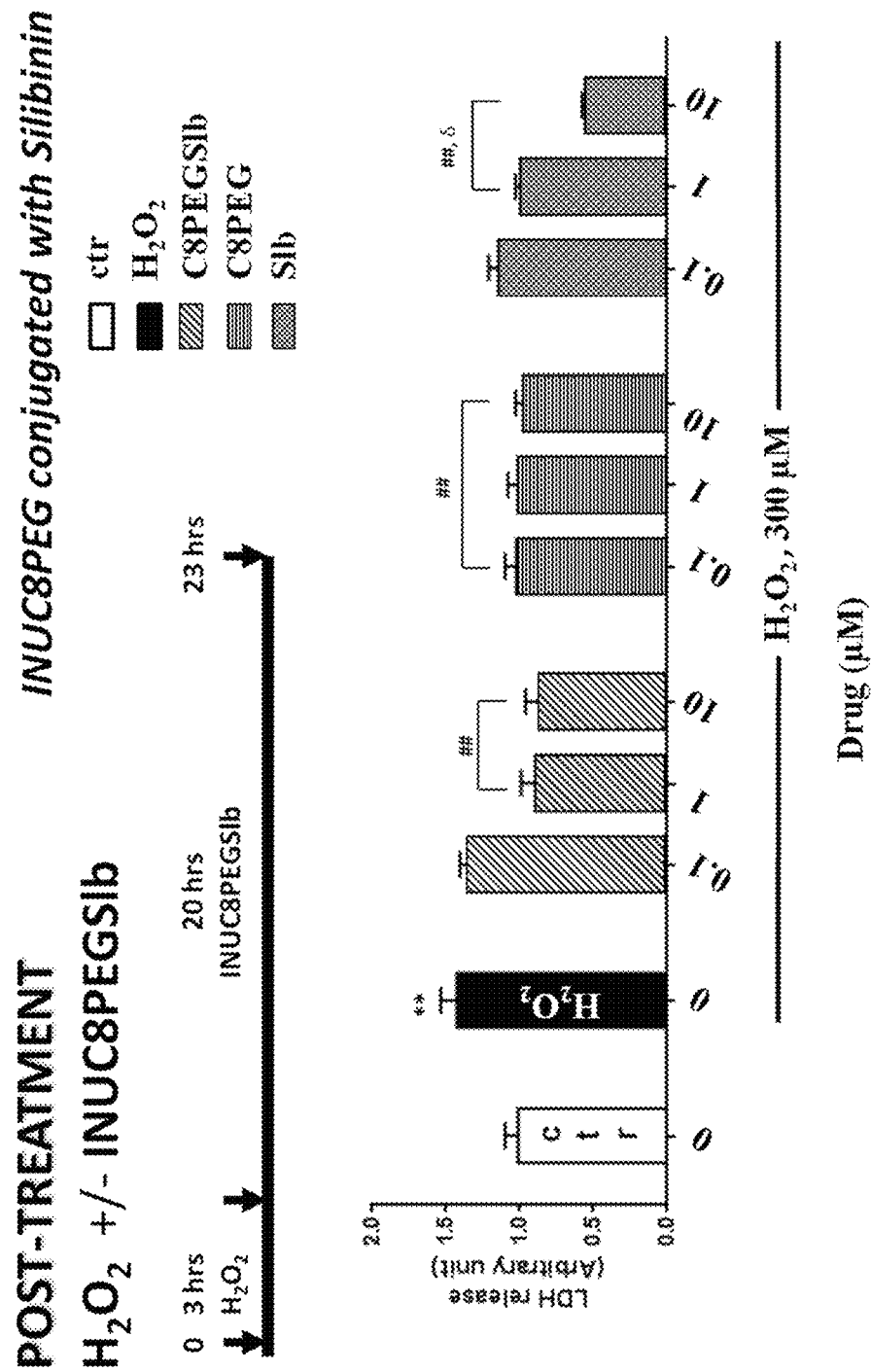

The micellar carriers INU-C8 and INU-C8-PEG conjugated with silibinin or with sorafenib tosylate were evaluated for the protective effect on retinal cells exposed to a pretreatment of 20 h and then insulted with $H_2O_2$ to induce an oxidative stress. The empty and conjugate INUC8PEG carrier shows a protective action greater than the carrier without PEG, however only the carrier INUC8PEG conjugated with silibinin or with sorafenib is able to cause a decrease in the LDH release at higher concentrations due to the presence of PEG. By way of example, FIG. 5A and FIG. 6 show the experimental test data of the system conjugated with the active ingredient sorafenib or silibinin, respectively.

In a post-treatment protocol, the retinal cells insulted for three hours with $H_2O_2$ and subsequently exposed to treatment with the INU-C8 and INU-C8-PEG systems conjugated with silibinin or sorafenib show a good ability of both carriers to revert the insult-induced damage. However, the INUC8PEG system conjugated with either active ingredient is more effective in inhibiting the $H_2O_2$-induced stress. By way of example, FIG. 5B and FIG. 6B show the experimental test data of the system conjugated with the active ingredient sorafenib or silibinin, respectively.

Figure 7:
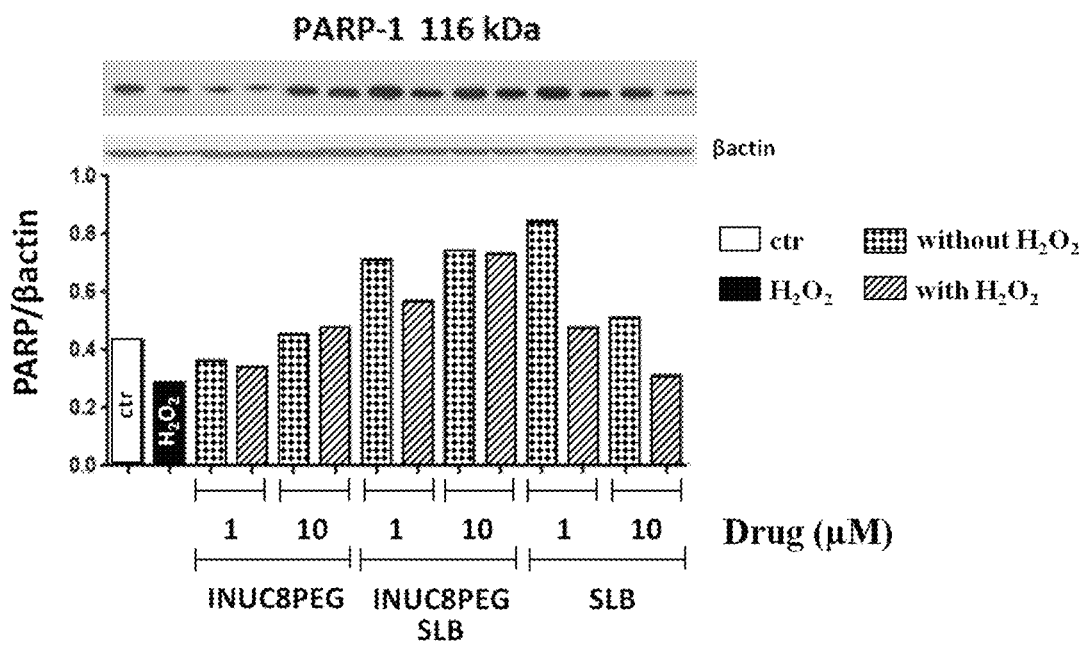
FIG. 7 shows the representative Western blotting performed on samples without (control, C) or with $H_2O_2$ (H), and treated or not with INUC8PEG (1 μM and 10 μM), with INUC8PEGSlb (1 μM and 10 μM) or with Slb (1 μM and 10 μM) Anti-PARP1 1:800 primary antibodies were used (Cell Signaling). The densitometric analysis of the bands (histograms) was normalized for β-actin.

Lysates of retinal cells exposed to post-treatment with the INUC8PEG system, empty or conjugated with silibinin, were analyzed by western blotting for the expression of the PARP-1 protein, a poly (ADP-ribose) polymerase of 116 kDa involved in DNA repair in response to environmental stress (*Calcium Overload Is A Critical Step In Programmed Necrosis Of Arpe*-19 *Cells Induced By High-Concentration $H_2O_2$* Guang-Yu Li et al., (2010) Biomedical And Environmental Sciences). In vivo and in vitro, PARP-1 is processed by Caspase 3 and Caspase 7 with the formation of a 24 kDa DNA-binding domain and an 89 kDa catalytic domain that participates in the apoptosis (*Importance of Poly (ADP-* ribose) *Polymerase and Its Cleavage in Apoptosis* F. J Oliver et al., (1998) J. Biol. Chem.). FIG. 7 shows a reduction in the PARP-1 protein following treatment with $H_2O_2$ which confirms the cell apoptotic status. Conversely, in the samples treated with the conjugated carrier, higher expression of PARP-1 is observed compared to the free carrier and Slb itself. The ability of INUC8PEG conjugated with Slb to inhibit the apoptosis induced by the oxidative damage is confirmed in a dose-dependent manner in the samples treated with $H_2O_2$. The post-treatment with free Slb reduces the apoptotic process, however with less efficiency than the conjugated carrier.

Example 4

Preparation of Calixarene Nanoparticles

As an example, the procedure and the experimental data obtained with the calix[4]arene derivative (compound 1)—loaded with silibinin, curcumin or latanoprost is described hereinafter.

Preparation

The amphiphilic calix[4]arene derivative bearing four dodecyl aliphatic chains at the lower edge of the macrocycle and four polar heads of choline at the upper edge (compound 1) was synthesized, with good yield, adapting a procedure described in literature for similar derivatives. The compound was characterized by NMR spectroscopy and mass spectrometry.

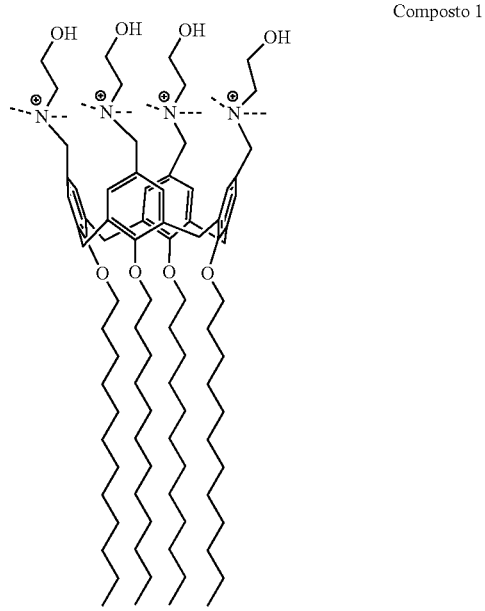

Composto 1

The assembly of the calixarene derivative in nanoaggregates occurs spontaneously. The simple dissolution in PBS (pH 7.4) provides a colloidal solution containing nanoaggregates with size, polydispersity index and zeta potential shown in table 6.

The drug loading was carried out by adding an excess of drug (molar ratio 1:5) to the colloidal solution as bottom body. The mixture was exposed to ultrasounds for 15 minutes and stirred in a shaker at 25° C., 200 rpm, for 2-3 days. The subsequent centrifugation at 4000 rpm for 30 minutes and filtration on GHP Acrodisc 0.2 μm filter provides a colloidal solution of nanoparticles loaded with silibinin. The freeze-drying of this solution, without the addition of cryoprotectants and using a standard freeze-dryer, provides a white powder that resuspended in water restores the colloidal solution of nanoparticles loaded with drug. The re-filtration of the colloidal solution on GHP Acrodisc 0.2 μm filter and subsequent HPLC analysis to determine the % DL show that following freeze-drying, the system retain the incorporated drug load (table 6).

Size Determination and Zeta Potential Measurement

The average diameter, polydispersity index (PDI) and zeta potential of calixarene nanoparticles loaded and not with silibinin were measured using a Zetasizer Nano ZS-90 (Malvern Instrument), the reading was made at an angle of 90° with respect to the incident ray and analyzed in triplicate. The results obtained for average diameter, PDI and zeta potential are given in Table 6.

TABLE 6

Average hydrodynamic diameter, polydispersity index (PDI), zeta potential of the calixarene nanoaggregates.

DLS (in PBS, pH 7.4)

|  | Z-average (nm) | PDI | Potential ζ (mV ± SD) |
| --- | --- | --- | --- |
| Calixarene nanoparticle (NP) | 44.3 | 0.29 | 24 |
| Calixarene-silibinin nanoparticle | 77.8 | 0.3 | 23.4 |
| NP-silibinin POST-freeze-drying | 81.5 | 0.35 | 23 |

Determination of Drug Loading (% DL) of the Calixarene Nanoparticle

To determine the amount of silibinin loaded into a colloidal solution containing 1 mg/mL of calixarene nanoparticle, an aliquot of the solution was diluted with methanol and analyzed by HPLC. The amount of drug was measured considering the absorption band of silibinin at 288 nm. The amount of drug was also measured at the UV spectrometer considering the 327 nm band of silibinin in PBS.

The results obtained in terms of % DL (expressed as a percentage ratio between weight of the active ingredient loaded and weight of the active ingredient loaded+weight of the nanoparticle) was found to be equal to 10-11%.

Release in of Silibinin From the Calixarene NP in PBS at pH 7.4

The release of silibinin in phosphate buffer at pH 7.4 was investigated in vitro at 37° C. with incubation times in the range between 0 and 12 hours by dialysis. The results obtained have shown that the system slowly releases the drug up to a maximum of 6.5% w/w within 12 hours (FIG. 7). The slow release might be advantageous for the purpose of drug delivery in the pathological site.

Stability Study of the Calixarene Nanoparticle Loaded With Silibinin in PBS at pH 7.4

The stability of calixarene nanoparticles loaded with silibinin was assessed by keeping the colloidal solutions in PBS at 25° C. Controls at 7 and 14 days from the preparation show size, PDI and % DL values virtually unchanged (table 10). The stability of the formulation is an important pharmacological (e.g. achievement of the pathological sites at the back of the eye) and industrialization requirement.

TABLE 10

Stability of the colloidal solution of calixarene nanoparticle-silibinin after 7 and 14 days at 25° C.

| Incubation time | Average diameter (nm) | PDI |
|---|---|---|
| Time 0 | 77.8 | 0.3 |
| 7 dd | 78.8 | 0.3 |
| 14 dd | 80.6 | 0.3 |

Figure 8:
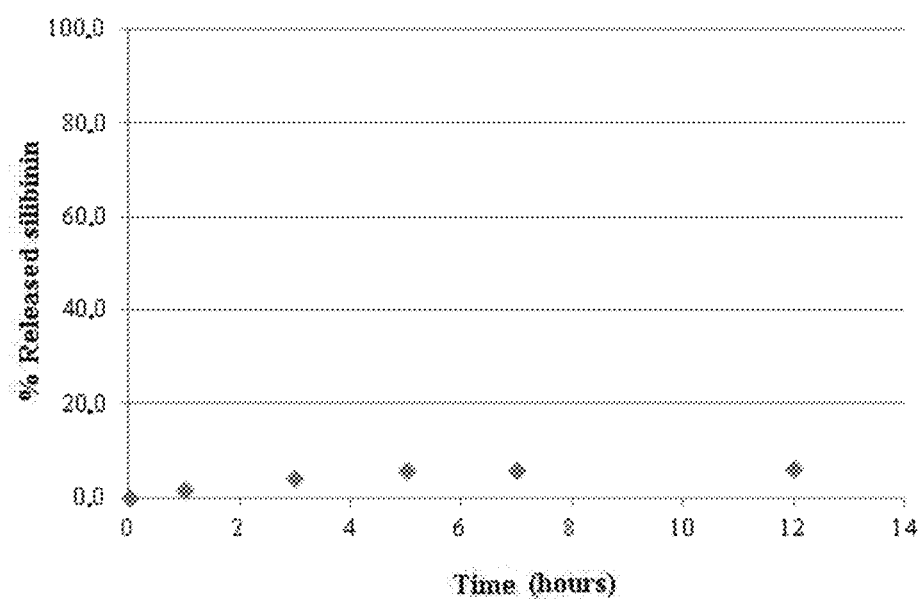
FIG. 8 shows the percentage of silibinin released by the calixarene nanoparticles in PBS at pH 7.4 as a function of the incubation time.

Following preliminary investigations of the calixarene-choline carrier conjugated with silibinin in ARPE-19 cells, it was determined that concentrations of the carrier, either free or conjugated with Slb included in range 0.01-1 µM and incubated for 20 hours caused no toxicity. Then, the effects of the conjugated and empty system were tested using the compound $FeSO_4$ as oxidative insult, with changes in the cellular redox status. Over 24 hours of incubation, the cells are pre-treated for 20 h and then exposed to insult with 50 µM $FeSO_4$ for three hours ["Pretreatment" 20 h drug+3 h insult]. The viability test conducted to evaluate the toxicity and the ability of protection from damage of the carrier in question is to assess the release of LDH in the culture medium. FIG. 8A shows a dose curve of the carrier conjugated with Slb (CalixSlb), of the empty carrier (Calix) and of silibinin alone (Slb) in ARPE cells subjected or not to insult with 50 µM $FeSO_4$. It is noted that Slb reduces the release of LDH, while Calix Slb and the empty do Calix do not significantly change the release of LDH of ARPE-19 cells. Conversely, when the cells are exposed to $FeSO_4$ (50 µM), Calix Slb shows good potential in reducing the release of LDH, an effect not observed in the samples treated with Calix and Slb individually. These results suggest that calix and Slb may together prepare the cells towards a protection against changes in the redox status. In subsequent experiments, the effects of post-treatment with calixarene based compounds were tested. Therefore, cells were treated with 50 µM $FeSO_4$ for 5 hours and incubated for 20 hours with the various compounds. As shown in FIG. 8B, CalixSlb protects against insult even in post-treatment conditions and the effect is confirmed as a synergic action of the two compounds that are individually able to protect from the redox status alteration.

Figure 9:
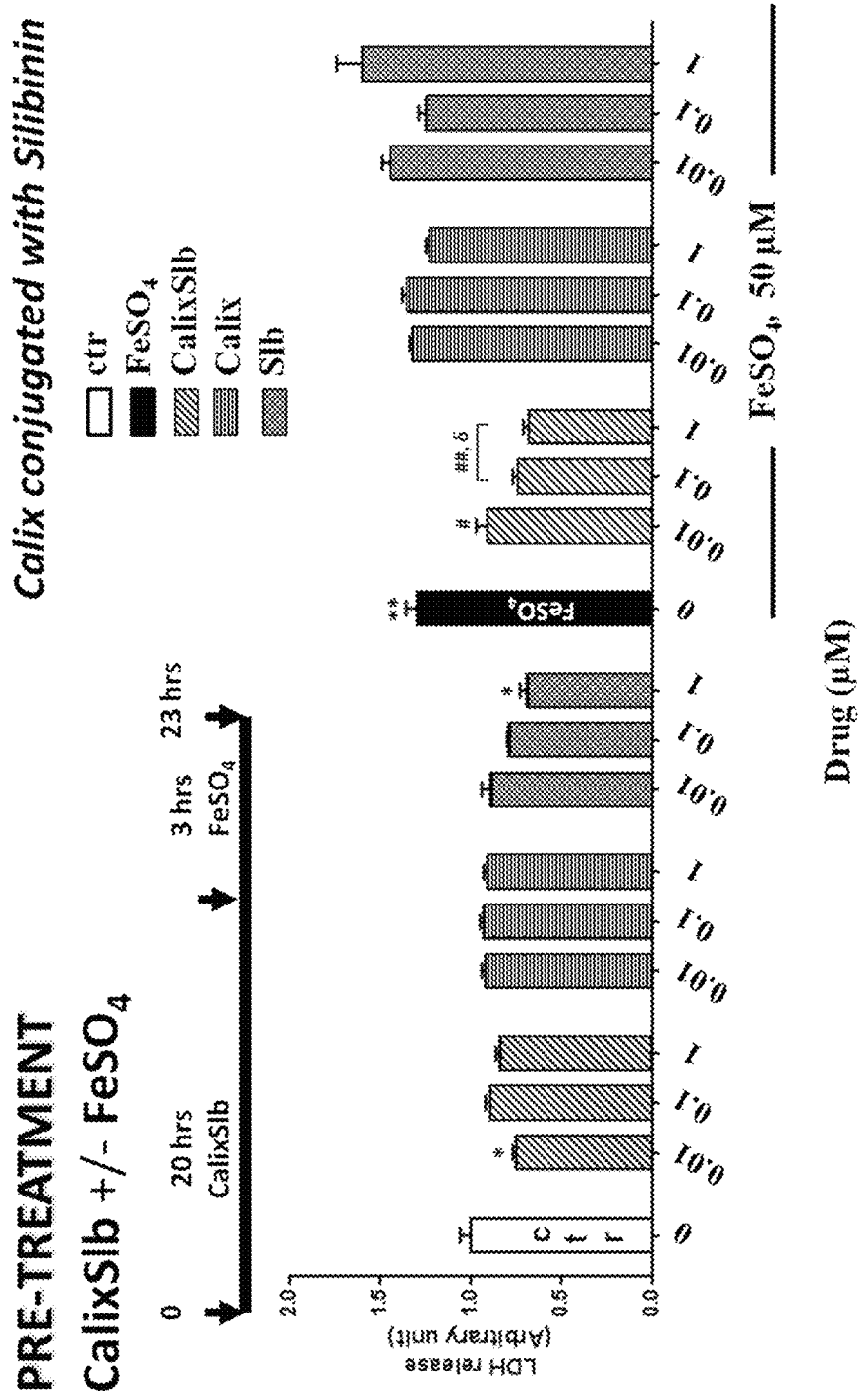
FIG. 9A shows the effect on ARPE-19 retinal cells pretreated for 20 hours with the Calixarene-Silibilin system (CalixSlb), with the empty carrier (calix) and with silibinin alone, and thereafter exposed to 50 μM $FeSO_4$; quantification of LDH release into the medium.
FIG. 9B shows the effect on ARPE-19 retinal cells treated with $FeSO_4$ 50 μM for 5 hours and post-treated for 20 hours with the Calixarene-Silibinin system (CalixSlb), with the empty carrier (calix) and with silibinin (Sib) alone; quantification of LDH release into the medium.
Figure 9:
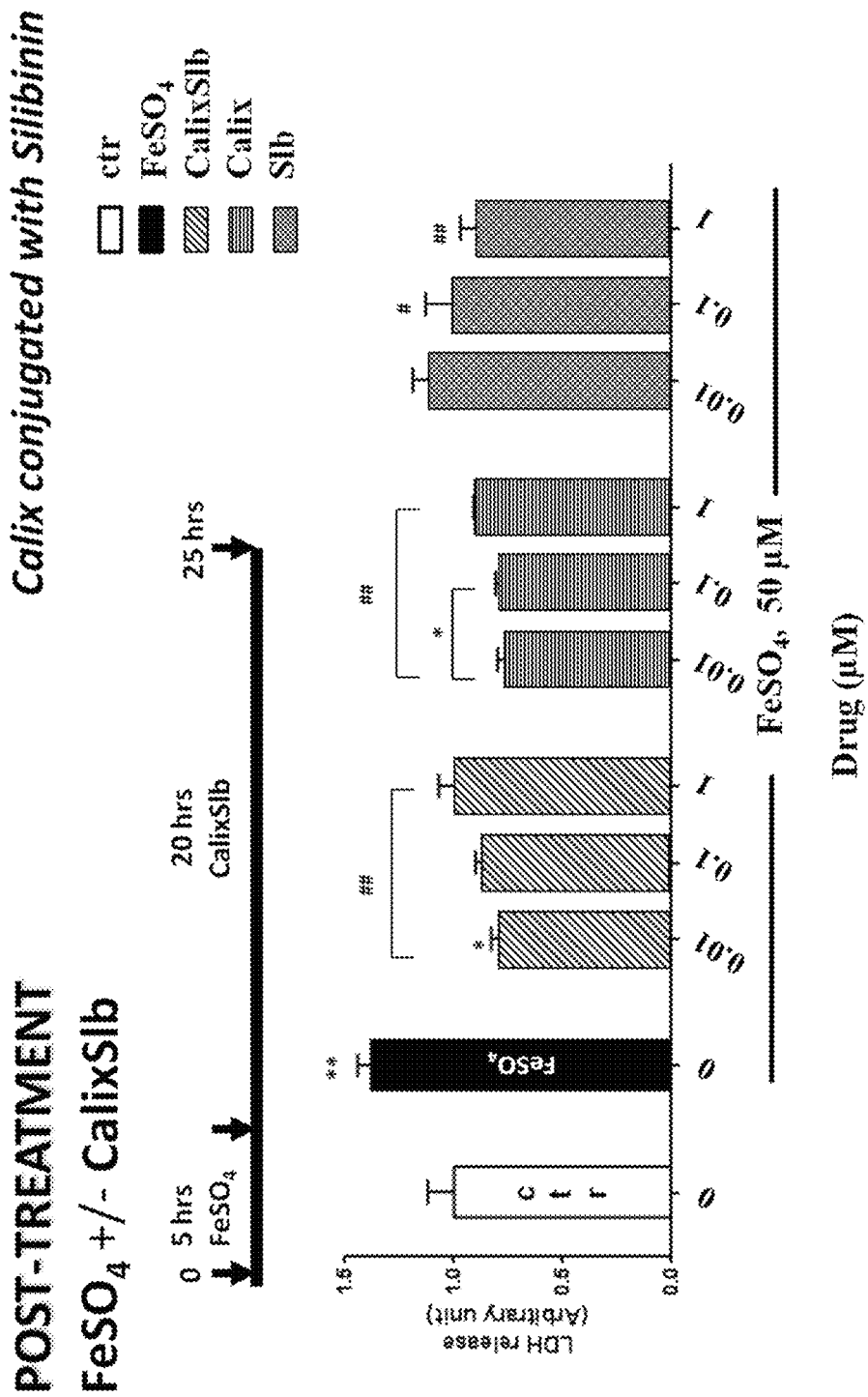

FIG. 9A shows the western blot analysis of VEGF which shows a reduction in the expression levels of soluble VEGF after insult with $FeSO_4$, this reduction is annulled by the empty Calix, by Slb and by Calix Slb at the concentration 1 µM of Calix Slb. In fact, Calix Slb itself is able to increase the levels of VEGF. These results are in agreement with the observations reported by Lin et al. (*Silibinin inhibits VEGF secretion and age-related macular degeneration in a hypoxia-dependent manner through the PI-3 kinase/Akt/mTOR pathway* C H Lin et al., (2013) British Journal of Pharmacology) on the inhibition of VEGF secretion under hypoxic conditions of ARPRE cells and pretreatment with the drug. The lack of secretion leads to the lack of free VEGF that cannot act as a self-regulator of (autocrine signalling) with concomitant decrease of the angiogenic process.

Cathepsin D is an intracellular aspartyl protease, synthesized in the endoplasmic reticulum as pre-pro-enzyme that is processed up to generate active fragments. According to the cellular environment in which it resides, it can induce or inhibit apoptosis through different mechanisms. The 48 kDa fragment is an active intermediate form from which two additional active fragments are generated; therefore, its reduction is associated with the activation of the proteolytic process, vice versa its increase is indicative of an inhibition of apoptosis. In the presence of oxidative stress, the activation of cathepsin D may activate caspase 8 which in turn activates caspase 3, leading to cell death (*Regulatory role of cathepsin D in apoptosis*, A. Minarowska et al., (2007) Folia Histochemica et Cytobiologica) (*Caspase-8-mediated apoptosis induced by oxidative stress is independent of the intrinsic pathway and dependent on cathepsins* H. K. Baumgartner et al., (2007) Am J Physiol Gastrointest Liver Physiol.). As shown in FIG. 9B, the exposure of cells to $FeSO_4$ results in a reduction of the 48 kDa band of cathepsin D. The post-treatment with Calix or Slb increases the expression levels of cathepsin D, but the greater increase in the protein is observed in samples treated with Calix Slb, confirming the potentiating effect of the conjugate in terms of protective activity, which is detected as inhibition of the apoptotic process in which cathepsin D is involved.

The calixarene carrier compound (1) lends itself to load a variety of hydrophobic molecules, in this invention as an example, it was loaded with curcumin and latanoprost in addition to silibinin. The above active ingredients are characterized by low water solubility, easy chemical and enzymatic degradation, low bioavailability. Curcumin and silibinin are natural substances that are used in a variety of conditions ranging from inflammation to cancer, latanoprost is a prostaglandin F2α analog used in the treatment of glaucoma, a condition that is still a leading cause of irreversible blindness in the world.

Also for these active ingredients, the loading of the active ingredient in the nanoaggregate compound (1) occurs through the phase solubility method with drug loading≥10%. The dosage of the active ingredient was performed by HPLC analysis and UV spectroscopy.

The nanoaggregate (compound 1) loaded with active ingredient was characterized by DLS and zeta potential measurements that showed that nano-dimensions, polydispersity index and surface loading are still suitable for drug delivery systems (table 11)

TABLE 11

Chemical and physico-chemical features of aggregate 1 loaded with active ingredient curcumin or latanoprost

| Chemical-physical requirements | Carrier-Curcumin | Carrier-Latanoprost |
|---|---|---|
| Dimensions ≤100 nm | Z average 82 nm, $D_H$ 113 nm | Z = 65.7 nm |
| Polydispersity ≤0.5 | 0.2 | pdi = 0.26 |
| Zeta potential ≠0 | 23 mV | |
| Stability in PBS at room temperature | DLS stable, [drug], LC over 15 days | DLS stable, [drug], LC after 4 months |
| Sterilizability | Filtration 0.2 µm | Filtration 0.2 µm |
| Drug loading % | 10% | 45% |
| Drug release % | 20-30% EtOH/ PBS 1-27% 24 h | |

Calixarene 1 increases the solubility of curcumin as well as of silibinin in aqueous medium by at least ten times.

Figures 10, 10B:
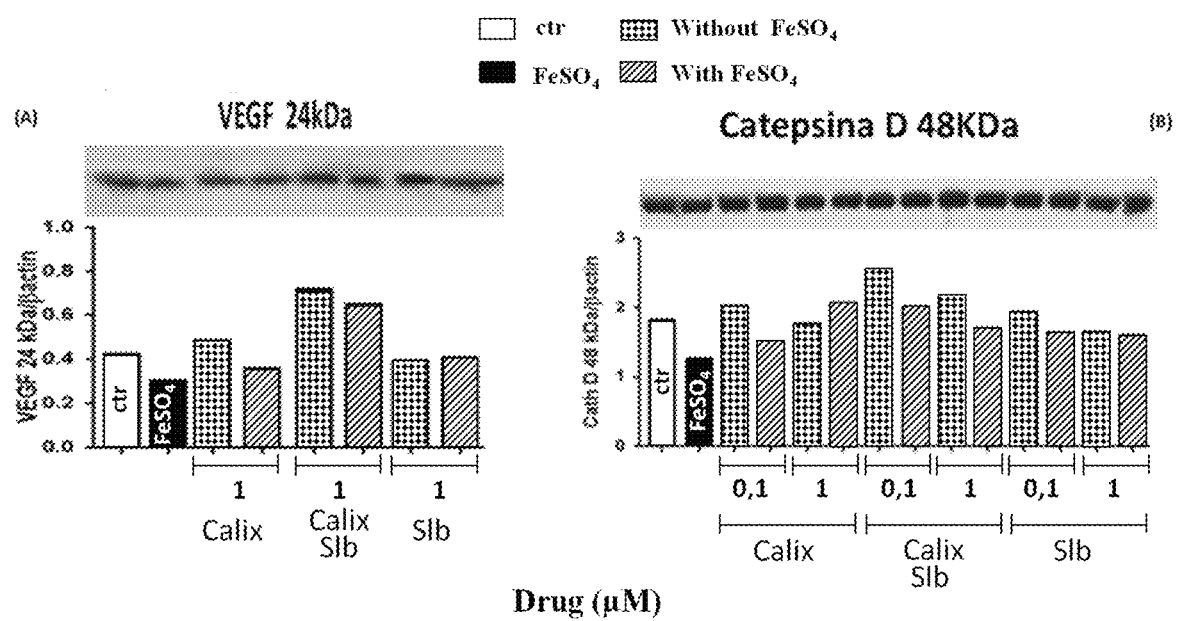
FIG. 10A/B shows the representative Western blotting performed on samples without (CTR) or with FeSO4 (Fe) and treated or not with Calix (1 μM), with CalixSlb (1 μM) or with Slb (1 μM). Anti-VEGF 1:100 primary antibodies were used (Santa Cruz) (10A) and the representative Western blotting performed on samples without (CTR) or with FeSO4 (Fe) and treated or not with Calix (0.1 μM and 1 μM), with CalixSlb (0.1 μM and 1 μM) or with Slb (0.1 μM and 1 μM). Anti-cathepsin D 1:200 primary antibodies were used (Santa Cruz). The densitometric analysis of the bands (histograms) was normalized for β-actin (10B).

Calixarene 1 protects curcumin in PBS as a solvent, which shows a degradation of 80-90% in 30 min with 0.1 M PBS and in serum-free medium. (FIG. 10)

Calixarene 1 protects latanoprost from degradation (table 12) in PBS as a solvent at room temperature for over 6 months. This is an interesting result because it allows the production of an innovative formulation which unlike those currently on the market, is released from the cold chain and is free from preservatives.

TABLE 12

Stability of the colloidal calixarene-latanoprost solution
up to 4 months from preparation in PBS at room temperature:
size, pdi, latanoprost concentration

| giorni | Z average | | pdi | | [drug] | |
|---|---|---|---|---|---|---|
| | t.a. | 4° C. | t.a. | 4° C. | t.a. | 4° C. |
| 0 | 69.2 | 69.2 | 0.26 | 0.26 | 52 | 54 |
| 6 | 72.0 | 72.3 | 0.30 | 0.29 | 54 | 56 |
| 14 | 69.0 | 68.2 | 0.30 | 0.32 | 54 | 57 |
| 34 | 72.6 | 69.6 | 0.34 | 0.33 | 55 | 56 |
| 48 | 66.9 | 66.3 | 0.35 | 0.31 | 52 | 54 |
| 92 | 76.8 | 78.0 | 0.39 | 0.37 | 53 | 58 |
| 130 | 65.3 | 68.9 | 0.31 | 0.29 | 50 | 53 |

Figure 11:
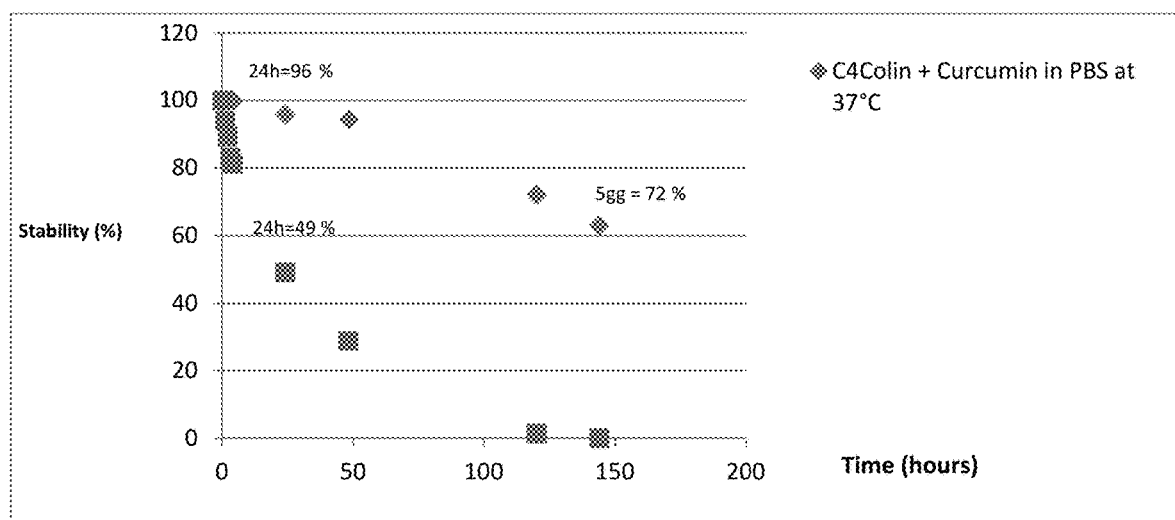
FIG. 11 shows the protective effect of the calixarene system towards the active ingredient curcumin, for which a degradation of 90% in 30 min in 0.1 M PBS and in serum-free medium is shown for comparison.
Figure 12:
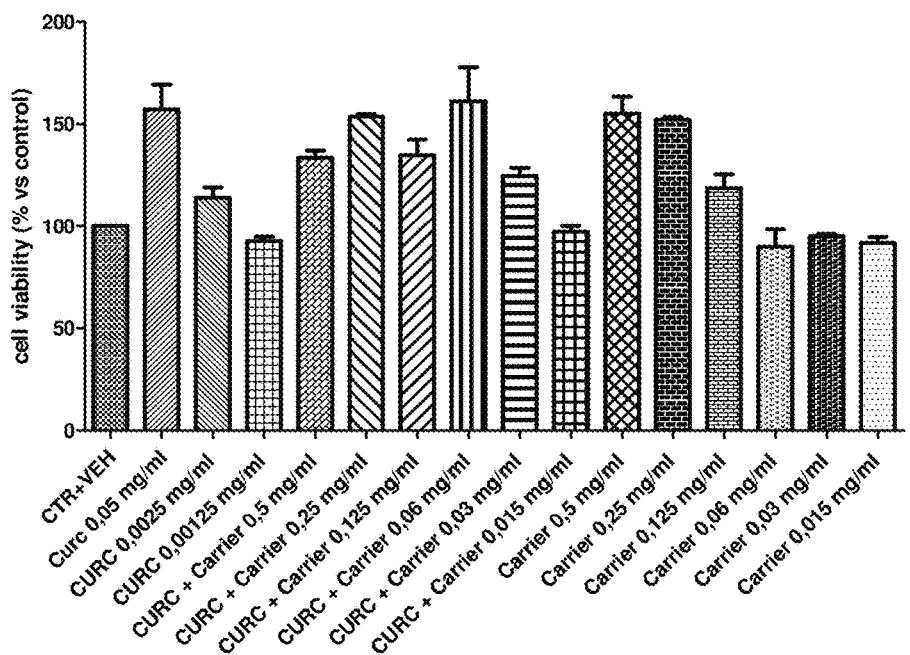
FIG. 12 shows the results of the cytotoxicity tests on SIRC corneal cells following treatment with curcumin, calixarene system and calixarene-curcumin system.

The colloidal solutions of calixarene 1, calixarene loaded with active ingredient and active ingredient alone were tested for cytotoxicity: SIRC corneal cells (FIG. 11), J774 macrophages (FIG. 12) and ARPE retinal cells. The results showed good biocompatibility of calixarene and of the calixarene-active ingredient combination on all cell types tested.

Figure 13:
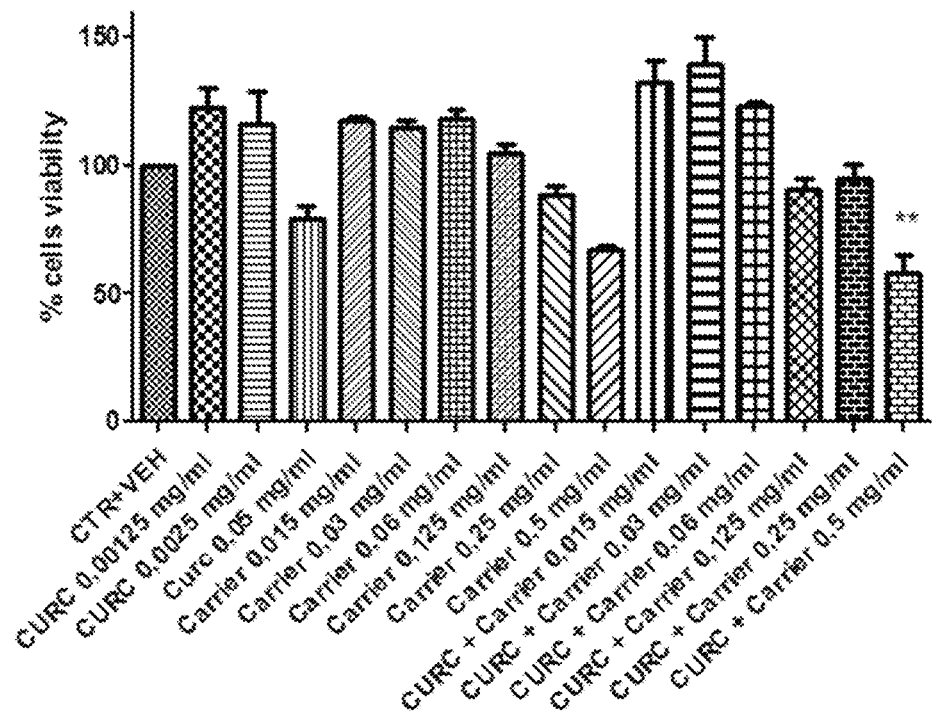
FIG. 13 shows the results of the cytotoxicity tests MIT assay on J744 macrophages of curcumin, calixarene and calixarene-curcumin.
Figure 14:
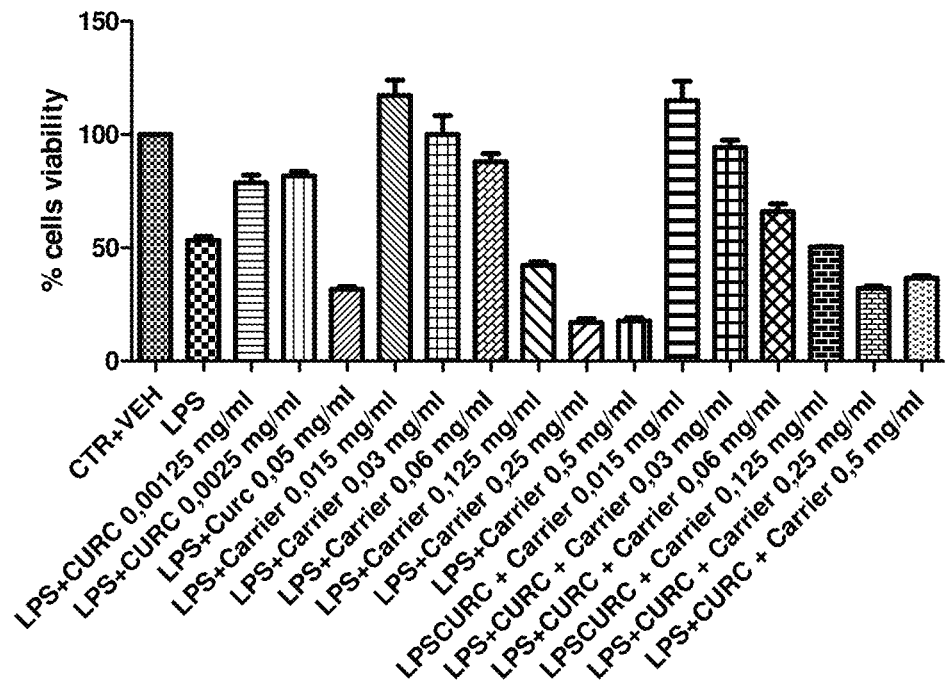
FIG. 14 shows the vitality of J744 macrophages stimulated with LPS and pre-exposed to treatment with curcumin, calixarene system and calixarene-curcumin system.

The anti-inflammatory activity of the colloidal solutions of calixarene 1, calixarene-curcumin and curcumin alone was tested in vitro on J774 cells subjected to inflammatory stress by insult with LPS. In particular, J774 cells were stimulated with lipopolysaccharide (LPS) at a concentration of 10 μg/mL for 24 hours, stimulation with LPS induces the activation of inflammatory processes such as NFκB nuclear translocation and cytokine production, if not also release of nitrites and nitrosative stress. The cell viability was then evaluated following stimulation with LPS (10 μg/mL for 24 hours) and 2-hour pretreatment of the delivery systems being studied at the different concentrations. The cell viability following stimulation with LPS was reduced by 50%, treatment with the substances being examined such as curcumin, carrier and carrier associated with curcumin were able to restore the cell viability, almost returning it to the control levels, except for the higher concentrations that already appeared to be toxic to insulted cells (FIG. 13). The anti-inflammatory activity of the delivery systems was then evaluated through the Western Blot analysis. First, the degradation of IκBα (FIG. 14) and the consequent NFκB translocation to the nucleus (FIG. 15) were observed, which leads to the production and activation of pro-inflammatory genes such as those encoding cytokines. The results show that the stimulation with LPS (10 μg/mL for 30 min) significantly increases the degradation of IκBα and the subsequent translocation of NFκB to the nucleus (whose levels are significantly increased, as can be seen in FIG. 15). On the contrary, the pre-treatment with the delivery systems is able to significantly reduce the degradation of IκBα and NFκB translocation (FIG. 15). The NFκB activation involves the production of proteins and inflammatory mediators such as cyclooxygenase 2 (COX-2) and inducible nitric oxide synthase (iNOS) and consequent increase in the production of nitrites. Through the Western blot analysis, it was observed that the stimulation with LPS (10 μg/mL for 24 hours) significantly increases both the level of iNOS and of COX-2. Pre-treatment with curcumin, carrier and carrier associated with curcumin reduces significantly and in a dose-dependent manner the levels of iNOS and COX-2 (FIG. 16)

The calixarene derivative not only carries out its activity as a carrier but also has anti-inflammatory activity on the macrophages subjected to inflammatory stress with LPS.

The tests conducted showed an anti-inflammatory activity of calixarene loaded with curcumin>>calixarene>>curcumin alone.

With the aim of verifying the effectiveness of the calixarene system loaded with the active ingredient to the eye site of interest, an experiment was conducted in vivo with an Uveitis model. Uveitis was induced in 160-180 g Lewis rats by single subcutaneous injection in the hind paw of 200 ig of the LPS endotoxin from Salmonella Minnesota diluted in 0.2 mL PBS, pH 7.4. The control group received only 0.2 mL of PBS in the hind paw. The rats were divided into treatment groups (calixarene system, calixarene-silibinin, silibinin alone, calixarene-curcumin and curcumin alone); pre-treated by topical administration for three days before the induction of uveitis, and later to the point of sacrifice, which occurred for some animals at 16 and others at 72 hours after the injection of the endotoxin. The eyes were enucleated for histological and immunohistochemical analysis. The aqueous humor was also taken for protein dosing. The histological analysis of the eye tissues from animals injected with LPS showed signs of severe uveitis with a strong infiltration of neutrophils. In animals treated with carrier alone, the degree of inflammation was not reduced. Treatment with silibinin showed a decreased but not significant ocular inflammation while the association of the calixarene+silibinin system reduced the damage.

However, treatment with curcumin and in particular with the calixarene+curcumin combination significantly decreased the histologic damage. No ocular inflammation was observed in the sham group.

Figure 17:
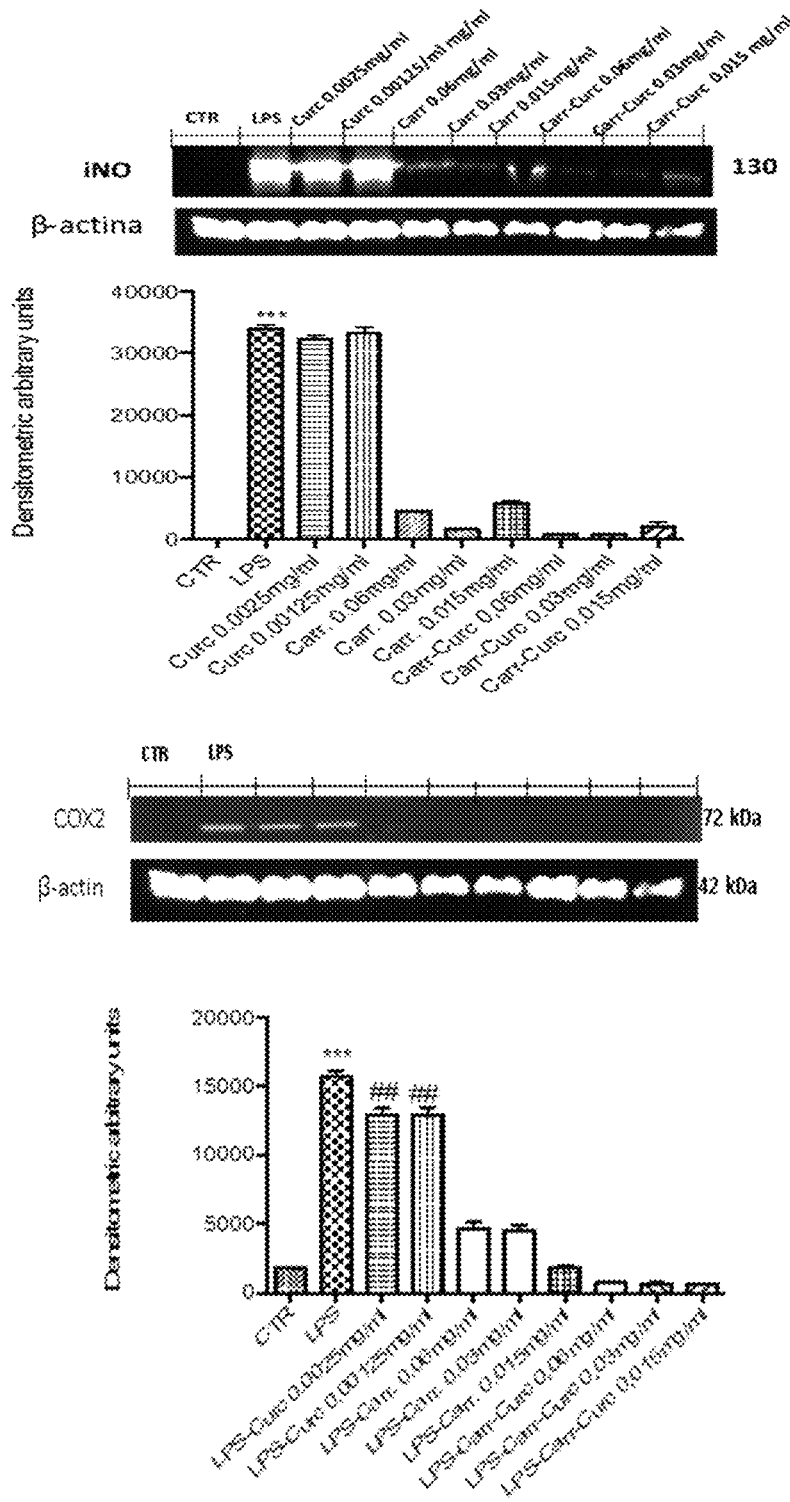
FIG. 17 shows the expression of iNOs and COX2 in J744 macrophages subjected to stress from LPS and their reduction in the presence of treatment with curcumin, calixarene 1 and calixarene-curcumin.

Moreover, no significant difference was observed between the groups at 16 h and 72 h. By way of example, the graph that summarizes the histological score recorded for the various groups at time 72 h is shown (FIG. 17A). At 16 and 72 hours after injection of LPS, increased levels of protein were observed in the aqueous humor of animals injected with LPS. Treatment with the carrier alone did not result in a reduction in the protein levels in the eye tissue. Silibinin-treated animals showed a trend but not significant, while the calixarene+silibinin system combination significantly reduced the level of proteins in the aqueous humor. However, curcumin and the calixarene+silibinin system combination most effectively determined the reduction of proteins in the ocular tissue. The samples taken at 16 h and at 72 h showed a similar trend in all experimental groups, by way of example, the graph with the protein dosage found at time 72 h for the various treatment groups is shown (FIG. 17B).

In order to verify the effectiveness of the calixarene system loaded with latanoprost, an in vivo experiment was set up with an ocular hypertension model induced in Brown Norway rats by episcleral vein cauterization (EVC).

The treatments were carried out once a day by instilling 12 μL/eye (left eye); the executive protocol involved a single administration treatment for the time course of the carrier system with the active ingredient, during which measurements of the intra ocular pressure (IOP) were taken after 1 h, 3 h, 5 h, 7 h, 24 h, 30 h and 48 h; and a chronic administration for seven consecutive days during which the measurement of IOP was evaluated every 24 h before the next instillation.

Figure 18:
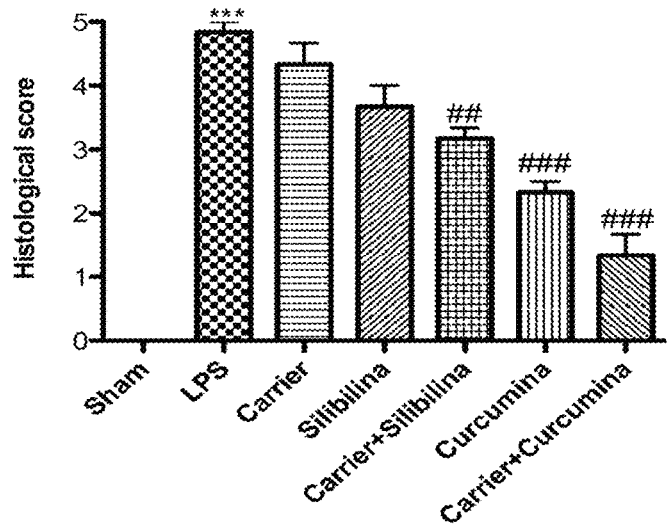
FIG. 18A shows the results of the histological score and of the protein assay in aqueous humor of animals treated with silibinin incorporated or not in the calixarene system, with curcumin incorporated or not in the calixarene system in a model of uveitis.
FIG. 18B shows the results of the histological score and of the protein assay in aqueous humor of animals treated with silibinin incorporated or not in the calixarene system, with curcumin incorporated or not in the calixarene system in a model of uveitis.
Figure 18:
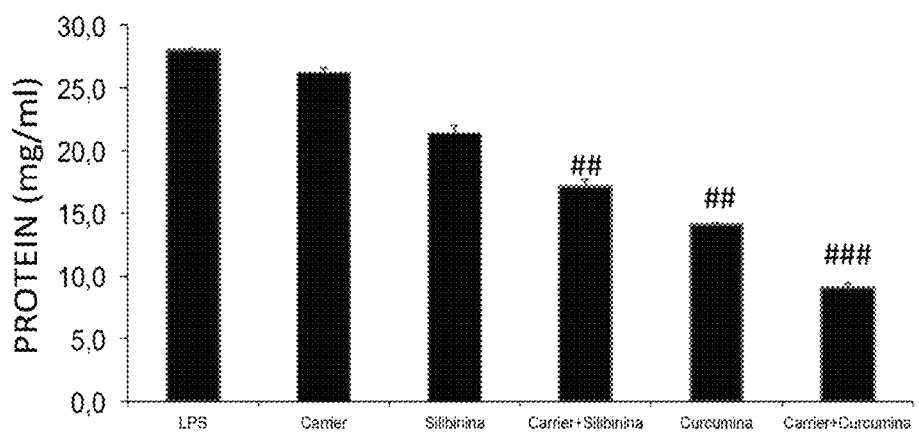
Figure 19:
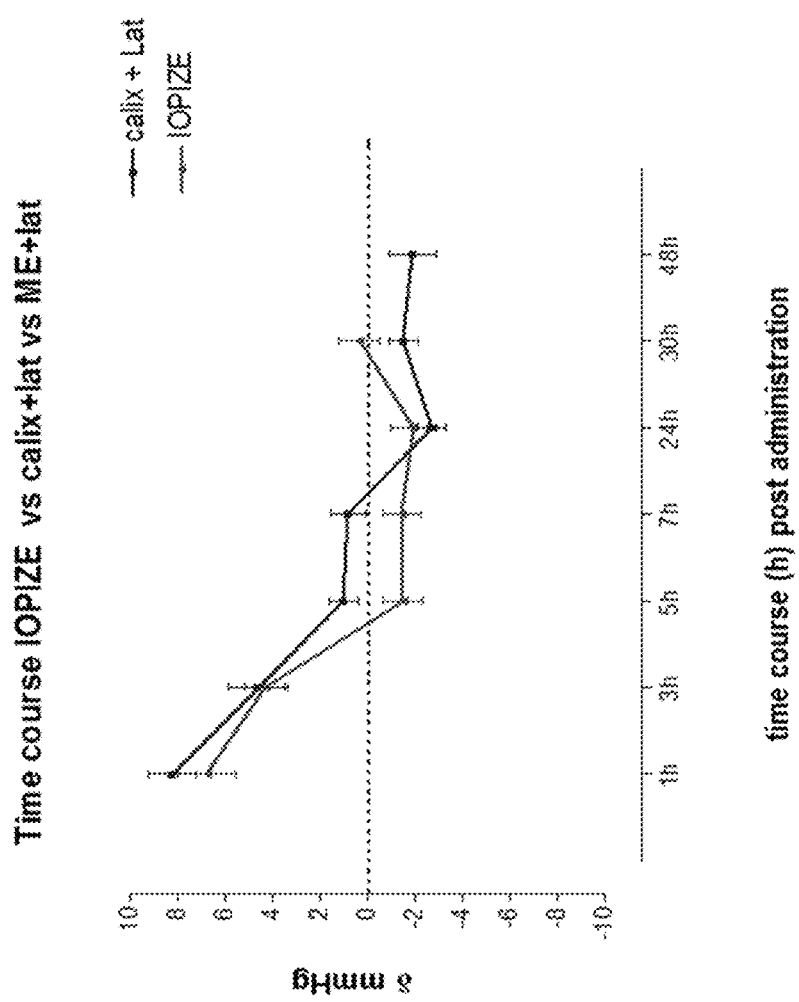
FIG. 19A shows the trends of the reduction in the intraocular pressure in a model of hypertonia after single administration (A) and after chronic treatment of the calixarene-latanoprost system and of the commercial product IOPIZE containing latanoprost.
FIG. 19B shows the trends of the reduction in the intraocular pressure in a model of hypertonia after single administration (A) and after chronic treatment of the calixarene-latanoprost system and of the commercial product IOPIZE containing latanoprost.
Figure 19:
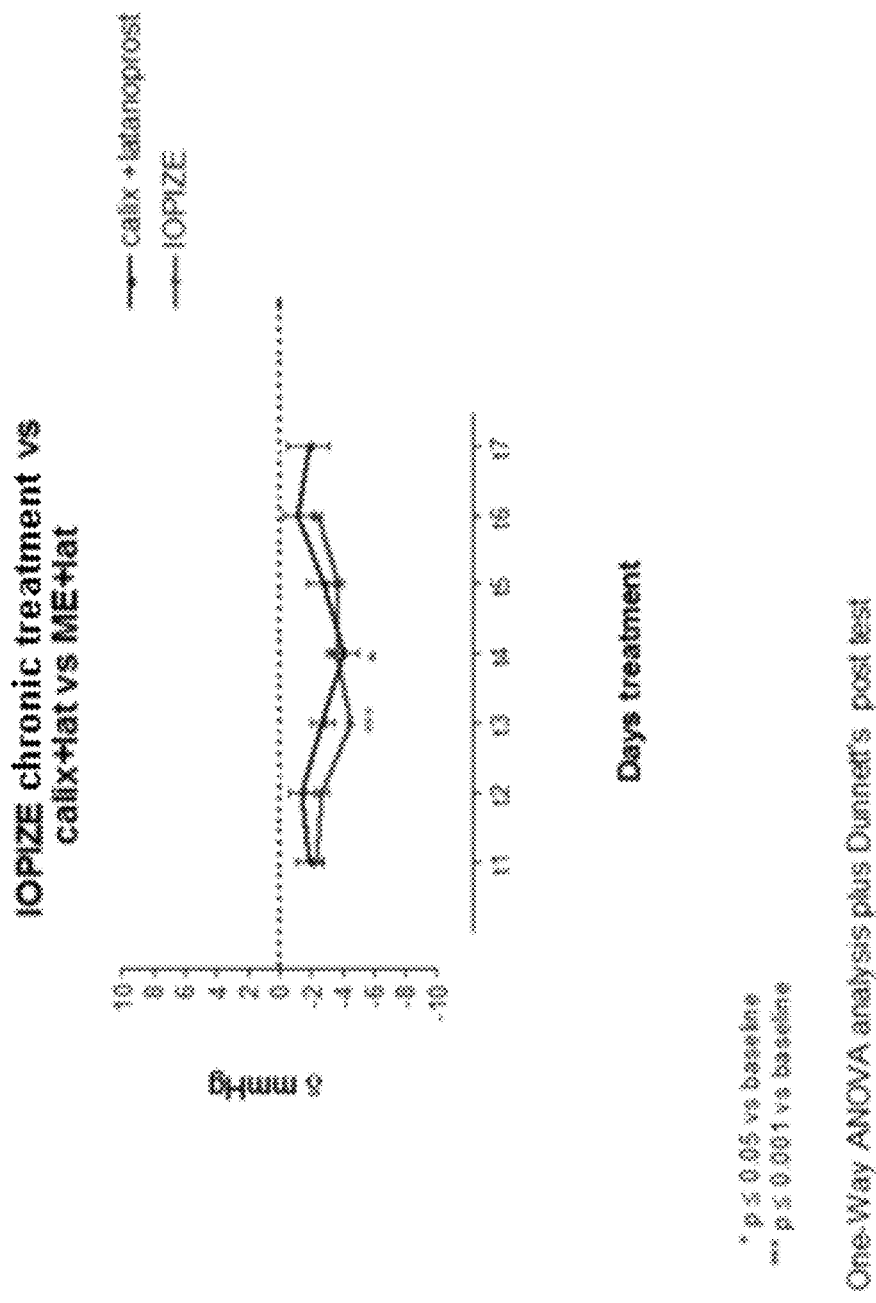

For each treatment group were made, each of which consisting of ten animals; the average IOP measurements recorded at the different time points were compared with the average value of the baseline, previously calculated. The graphs (FIG. 18A/B) show the trend of lowering intraocular pressure (IOP) upon treatment with Calix+latanoprost compared to the commercial product (IOPIZE) both after single administration following the time course at different time points (FIG. 18A), and following chronic treatment for seven days (FIG. 18B).

The trend of pressure variation for the two treatments is quite similar, both in the case of the calixarene-latanoprost system and in the case of the product IOPIZE, a paradox effect of latanoprost is observed during the first hours immediately following the administration and consisting of a marked increase in the IOP, this effect known in literature is typical in rats (*Latanoprost-induced changes in rat intraocular pressure: direct or indirect?* Husain S et al. *J Ocul Pharmacol Ther.* (2008); Effects of latanoprost on rodent intraocular pressure. Husain S et al. Exp Eye Res. (2006)), then a gradual lowering of pressure occurs which reaches its peak only after 24 h to then tend to increase. Chronic treatment with the administration every 24 h allowed a lowering of IOP which reaches its highest point of bending around the fourth day with the calixarene-latanoprost system. The calixarene system compared to commercial products offers the advantage of releasing the product from the cold chain, of formulating the product without preservatives while maintaining the effectiveness of the active ingredient.

The invention claimed is:

1. A method for the treatment of ocular diseases comprising the topical application of formulations comprising a member selected from the group consisting of silibinin, sorafenib, and curcumin incorporated in a compound of a formula selected from the group consisting of Formula (A):

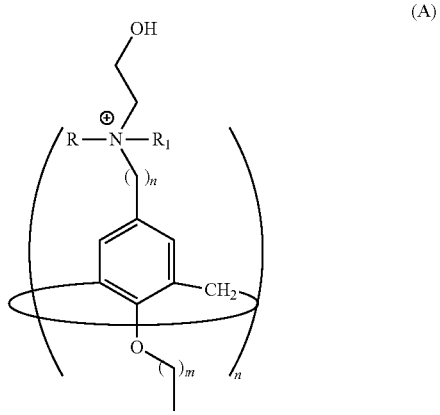

(A)

wherein:
R=$CH_3$, $(CH_2)_xCH_3$, $(CH_2)_xOH$
$R_1$=$CH_3$, $(CH_2)_xCH_3$, $(CH_2)_xOH$
wherein
x=1-3
n=4, 6, 8
m=2-15
and wherein when R=$R_1$=$CH_3$ m is different from 2-9, and Formula (1):

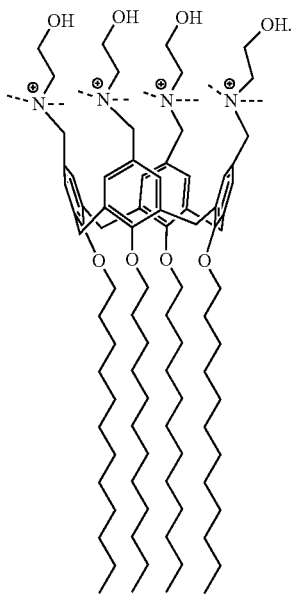

said ocular diseases selected from choroidal neovascularization (CNV), age-related macular degeneration (AMD), macular edema, neovascular glaucoma, macular edema, retinopathy of prematurity (ROP), diabetic retinopathy (DR), uveitis, endophthalmitis, retinitis, choroiditis and chorioretinitis.

2. The method of claim 1, wherein said compound of formula (A) or said compound of formula (1) have an average diameter in the range between 50 and 200 nm with a polydispersity index below 0.5.

3. The method of claim 1, wherein said formulation comprises said member in an amount in the range between 1 and 15% w/w.

* * * * *